US006753191B2

(12) United States Patent
Asher et al.

(10) Patent No.: US 6,753,191 B2
(45) Date of Patent: Jun. 22, 2004

(54) POLYMERIZED CRYSTALLINE COLLOIDAL ARRAY CHEMICAL SENSING MATERIALS FOR USE IN HIGH IONIC STRENGTH SOLUTIONS

(75) Inventors: Sanford A. Asher, Pittsburgh, PA (US); Chad E Reese, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 110 days.

(21) Appl. No.: 09/953,646

(22) Filed: Sep. 17, 2001

(65) Prior Publication Data

US 2002/0164823 A1 Nov. 7, 2002

Related U.S. Application Data

(63) Continuation-in-part of application No. 09/753,592, filed on Jan. 3, 2001, now Pat. No. 6,544,800, which is a continuation of application No. 09/111,610, filed on Jul. 7, 1998, now Pat. No. 6,187,599, which is a continuation of application No. 08/819,240, filed on Mar. 17, 1997, now Pat. No. 5,854,078, which is a continuation-in-part of application No. 08/743,816, filed on Nov. 6, 1996, now Pat. No. 5,898,004.

(51) Int. Cl.[7] .................. G01N 33/545; G01N 33/66; G01N 33/20; G01N 33/18; G01J 3/18
(52) U.S. Cl. .................. 436/531; 252/582; 436/73; 436/518; 436/529; 436/805; 435/6; 435/14
(58) Field of Search .................. 436/529, 531, 436/518, 805, 73; 435/6, 14; 252/582

(56) References Cited

U.S. PATENT DOCUMENTS

| | | | |
|---|---|---|---|
| 4,627,689 A | 12/1986 | Asher | |
| 4,632,517 A | 12/1986 | Asher | |
| 5,200,051 A | 4/1993 | Cozette et al. | |
| 5,226,902 A | 7/1993 | Bae et al. | |
| 5,266,238 A | 11/1993 | Haacke et al. | |
| 5,274,018 A | 12/1993 | Tanaka et al. | |
| 5,281,370 A | 1/1994 | Asher et al. | |
| 5,330,685 A | 7/1994 | Panzer et al. | |
| 5,338,492 A | 8/1994 | Panzer et al. | |
| 5,342,552 A | 8/1994 | Panzer et al. | |
| 5,368,781 A | 11/1994 | Haacke et al. | |
| 5,536,834 A | 7/1996 | Singh et al. | |
| 5,840,078 A | 11/1998 | Yerys | |
| 5,854,078 A | 12/1998 | Asher et al. | 436/133 |
| 5,898,004 A | 4/1999 | Asher et al. | |
| 6,187,599 B1 | 2/2001 | Asher et al. | |
| 6,544,800 B2 | 4/2003 | Asher | 436/531 |

OTHER PUBLICATIONS

Kitano et al., *Makromol. Chem., Rapid Commun.*, 12:227–233 (1991).
Vanderhoff et al., *Journal of Colloid and Interface Science* 28:336–337 (1968).
Pieranski et al., *Phys. Rev. Lett.* 50:900–903 (1983).
Flaugh et al., *Appl. Spectrosc.* 38:847–850 (1984).
Hirokawa et al., *J. Chem. Phys.* 81:6379 (1984).
Asher et al., "Crystalline Colloial Bragg Diffraction Devices: The Basis for a New Generation of Raman Instrumentation", *Spectroscopy* 1:26–31 (1986).
Rundquist et al., "Dynamical Bragg Diffraction From Crystalline Colloidal Arrays", *J. Chem. Phys.* 91:4932–4941 (1989).
Sheppard, "Design of a Conductimetric Microsensor Based on Reversibly Swelling Polymer Hydrogels", IEEE, 773–776 (1991).
Smits et al., *Adv. Colloid Interface Sci.* 42:33–40 (1992).
Kesavamoorthy et al., "Nanosecond Photothermal Dynamics in Colloidal Suspension", *J. Appl. Phys.* 71:1116–1123 (1992).
Asher et al., "New Nonlinear Bragg Diffraction Devices", *SPIE vol. 1626 Nonlinear Optics III*, 238–242 (1992).
Annaka et al., *Nature* 355:430–432, (1992).
Peula et al., *Colloids Surf. A* 77:199–208 (1993).
Dosho et al., "Recent Study of Polymer Latex Dispersions", *Langmuir*, vol. 9, No. 2, pp. 394–411 (1993).
Okano, "Molecular Design of Temperature–Responsive Polymers as Intelligent Materials", *Adv. Polym. Sci.* 110:179–197 (1993).
Bartlett et al., *Adv. Colloid Interface Sci.* 50:39–50 (1994).
McCurley, "An Optical Biosensor Using A Fluorescent, Swelling Sensing Element", *Biosensors and Bioelectronics* 9:527–533 (1994).

(List continued on next page.)

*Primary Examiner*—Mary E. Ceperley
(74) *Attorney, Agent, or Firm*—Baker Botts L.L.P.

(57) ABSTRACT

A novel method is disclosed wherein polymerized crystalline colloidal array (PCCA) chemical sensing materials are used to detect the presence of certain chemical species in high ionic strength solutions, such as bodily fluids. The PCCA sensors consist of a mesoscopically periodic array of colloidal particles polymerized into a hydrogel. The array of colloidal particles diffracts light in the visible spectral region due to the periodic spacing of the particles. The PCCA materials also contain molecular recognition components that bind to the chemical species being detected. The binding or the chelation of the chemical species of interest results in a Donnan potential that swells the hydrogel and in turn red shifts the diffracted light proportionately to the concentration of the chemical species. However, no significant red shift response may occur for PCCA chemical sensors in high ionic strength solutions containing chemical species of interest. Thus, the method of the present invention provides for incubating the PCCA chemical sensor in the sample solution, subsequently exposing the PCCA to a low ionic strength solution, such as pure water, and measuring the transient diffraction shift response of the PCCA upon the exposure to the low ionic strength solution. The non-chelated or non-bound ions (such as salt ions in high ionic strength solutions) diffuse out of the PCCA hydrogel more quickly than the chemical species ions bound to the molecular recognition component. Thus, the resulting transient PCCA diffraction red shift is proportional to the concentration of the chemical species in the sample solution. The present invention also discloses using the PCCA chemical sensors in an optrode for detecting certain chemical species in high ionic strength solutions, such as bodily fluids.

15 Claims, 17 Drawing Sheets

OTHER PUBLICATIONS

Asher et al., "Self Assembly Motif for Creating Submicron Periodic Materials: Polymerized Crystalline Colloidal Arrays", *J. Am. Chem. Soc. 116*:4997–4998 (1994).

Stoimenova et al., *J. Colloid Interface Sci. 176*:267–271 (1995).

Mitchie et al., *Opt. Lett. 20*:103–105 (1995).

Shibayama et al., *J. Chem. Phys. 102*:9392 (1995).

Schalkhammer et al., "The Use of Metal–island–coated pH Sensitive Swelling Polymers for Biosensor Applications", *Sensors and Actuators B*, vol. 24–25, pp. 166–172 (1995).

Sheppard et al., "Microfabricated Conductimetric pH Sensor", *Sensors and Actuators B*, vol. 28, pp. 95–102 (1995).

Tse et al., "Synthesis of Dyed Monodisperse Poly(methyl methacrylate) Colloids for the Preparation of Submicron Periodic Light–Absorbing Arrays", *Macromolecules 28*:6533–6538 (1995).

Asher et al., "Optically Nonlinear Crystalline Colloidal Self Assembled Submicron Periodic Structures for Optical Limiters", *Mat. Res. Soc. Symp. Proc. 374*:305–310 (1995).

Suzuki et al., *Chem. Abstr.*, vol. 125, 143841K (1996).

Jethmalani et al., *Chem. Mater. 8*:2138–2146 (1996).

Weissman et al., "Thermally Switchable Periodicities and Diffraction from Mesoscopically Ordered Materials", *Science 274*:959–960 (1996).

Asher et al., "Crystalline Colloidal Array Optical Switching Devices". *Nanoparticles in Solids and Solutions.* NATO ASI Series vol. 18, pp. 65–69 (1996).

Sunkara et al., "Design of Intelligent Mesoscale Periodic Array Structures Utilizing Smart Hydrogel", *Polymer Preprints 37*:453–454 (1996).

Kikuchi et al., "Glucose–Sensing Electrode Coated With Polymer Complex Gel Containing Phenylboronic Acid", *Anal. Chem. 68*:823–828 (1996).

Liu et al., "Fortuitously Superimposed Lattice Plane Secondary Diffraction from Crystalline Colloidal Arrays", *J. Am. Chem. Soc. 119*:2729–2732 (1997).

Pan et al., "Optically Nonlinear Bragg Diffracting Nanosecond Optical Switches", *Phys. Rev. Lett. 78*:3860–3863 (1997).

Kesavamoorthy et al., "Thermally Switchable Laser Diffracting Gels" in *Laser Applications in Material Science and Industry*, pp. 265–273 (1997).

English et al., *J. Chem. Phys. 107*:1645–1654 (1997).

Mafe et al., *Phys. Rev. Lett. 79*:3086–3089 (1997).

Holtz et al., "Polymerized Colloidal Crystal Hydrogel Films as Intelligent Chemical Sensing Materials", *Nature 389*:829–832 (1997).

Holtz et al., "Intelligent Polymerized Crystalline Colloidal Arrays: Novel Chemical Sensor Materials", *Anal. Chem. 70*:780–791 (1998).

Enlish et al., *Polymer 39*:5893–5897 (1998).

Reeder et al., *Sensors and Actuators B*, 52:58–64 (1998).

Yu et al., *Anal. Chem.*, 71:2998–3002 (1999).

de la Riva et al., *Anal. Chim. Acta*, 395:1–9(1999).

Lee et al., *J. Am. Chem. Soc.* 122:9534–9537 (2000).

Reese et al., *Journal of Colloid and Interface Science* 232:76–80 (2000).

Yarnitzky et al., *Talanta*, 51:333–38 (2000).

A

B

POLYMERIZED CRYSTALLINE COLLOIDAL ARRAY CHEMICAL SENSING MATERIALS FOR USE IN HIGH IONIC STRENGTH SOLUTIONS

This application is a continuation-in-part of U.S. patent application Ser. No. 09/753,592 of Asher, filed Jan. 3, 2001 now U.S. Pat. No. 6,544,800; which is a continuation of U.S. patent application Ser. No. 09/111,610, filed Jul. 7, 1998, now U.S. Pat. No. 6,187,599; which is a continuation of U.S. patent application Ser. No. 08/819,240, filed Mar. 17, 1997, now U.S. Pat. No. 5,854,078; which is a continuation-in-part of U.S. patent application Ser. No. 08/743,816, filed Nov. 6, 1996, now U.S. Pat. No. 5,898,004.

This invention was made with government support under Contract No. 1-R01-GM58821-01 awarded by the National Institute of Health, Contract No. 1-R01-DK55348-01 awarded by the National Institute of Health, Contract No. N00014-94-1-0592 from the ONR, and Contract No. DAAD19-99-0066 awarded by the United States Army. Therefore, the government has certain rights in the invention.

BACKGROUND OF THE INVENTION

The present invention generally relates to the use of polymerized crystalline colloidal array (PCCA) chemical sensing materials to detect concentrations of certain chemical species in high ionic strength solutions, such as bodily fluids or environmental testing. The PCCA materials are optical, hydrogel-based materials that act as sensors for certain chemical species because of the PCCAs' diffraction properties. More specifically, the present invention relates to utilizing the PCCA chemical sensing materials to detect the presence of varying concentrations of a chemical species, such as lead, in bodily fluids.

The development of novel methodologies for sensing the concentration of certain chemical species in high ionic strength solutions (such as bodily fluids) is technologically challenging because of the complexity of such solutions and because the concentrations of key chemical species within the fluids may be relatively low. Additionally, the high ionic strength of such solutions often decrease the sensitivity of certain chemical sensing methodologies already known in the art, such as the methods disclosed in U.S. Pat. No. 6,187,599 of Asher et al., the specification of which is hereby incorporated by reference herein in its entirety.

In disclosures such as U.S. Pat. No. 6,187,599, it has been demonstrated that PCCA materials can be used to detect low concentrations of chemical species such as $Pb^{2+}$ in low ionic strength solutions. Thus, a need exists for a method for measuring the presence of certain chemical species, even in high ionic strength environments.

The chemical sensing ability of the polymerized crystalline colloidal array materials disclosed in U.S. Pat. No. 6,187,599 results from changes in the volume of the hydrogel which embeds the crystalline colloidal array in response to a chemical species. These volume changes cause shifts in the wavelength of light diffracted by the PCCA, which results in a detectable color change.

The changes in volume of the hydrogel of the crystalline colloidal array result from changes in the free energy of the hydrogel. For example, immobilization of charge on the hydrogel due to the presence of a chemical species causes the hydrogel to undergo a volume phase transition. Specifically, when a polymerized crystalline colloidal array material is acting as a sensor for the presence of $Pb^{2+}$, it may comprise a chemical stimulus-recognition component having a crown ether which binds to $Pb^{2+}$. The binding of the $Pb^{2+}$ results in immobilization of charge and the hydrogel subsequently undergoes a volume change. Similarly, when a PCCA material is acting as a sensor for the presence of other chemical species, such as glucose, the glucose oxidase enzyme may be attached to the hydrogel as the chemical stimulus recognition component, and charge is immobilized on the reduced flavin of the glucose oxidase-upon binding of the glucose, causing a change in volume of the hydrogel.

However, these previously disclosed methods for using PCCA materials as chemical sensors have demonstrated that high ionic strength solutions decrease the magnitude of the hydrogel volume change. Thus, these prior art methods are limited in detecting the presence of certain chemical species in bodily fluids which have high ionic strengths. Thus, as previously noted, a need exists for a method that would allow PCCA chemical sensing materials to function effectively as sensors of certain chemical species including, but not limited to, $Pb^{2+}$, glucose, and cholesterol, even in high ionic strength environments.

With respect to utilizing PCCA chemical sensing materials to detect the presence of $Pb^{2+}$, developing a method for detecting $Pb^{2+}$ in high ionic strength solutions, such as bodily fluids, would address many medical and environmental problems, since $Pb^{2+}$ is such a serious medical and environmental toxin. Lead (specifically $Pb^{2+}$) can cause disease and death at concentrations as low as 700 parts per billion (ppb) in blood. Bodily concentrations of $Pb^{2+}$ as low as 100 ppb or 500 nM have been correlated with decreased IQ levels in children. Thus, universal screening of children for $Pb^{2+}$ in blood was enunciated as a public health goal by both the PHS and the Center for Disease Control in 1991.

Both the United States (Center for Disease Control) and international health organizations (World Health Organization) have set guidelines that recommend that lead in bodily fluids be measured with a detection limit of 10 $\mu g/dL$ or 480 nM, within a measuring range of (0–60) $\mu g/dL$ or (0–2.88) $\mu M$ lead, and with a precision of less than 2 $\mu g/dL$ or 10%, whichever is greater. Current estimates from the National Center for Health Statistics indicate that 3.2% of American children have blood $Pb^{2+}$ levels above 480 nM, while 20% of minority children in poverty have blood $Pb^{2+}$ levels above 480 nM.

Universal $Pb^{2+}$ screening was abandoned by the federal government in 1997 because of economic reasons, despite the large numbers of children at risk. Even when performed in large numbers, the laboratory cost for analyzing a single blood specimen for $Pb^{2+}$ is $8–15. The costs of drawing the blood, communicating the results, and more importantly, finding and retrieving the child, raise the price per case to $50 or more. Thus, a rapid, simple and inexpensive quantitative serum $Pb^{2+}$ test that could identify a child with an elevated $Pb^{2+}$ level while the child is still present in the office would reduce the costs dramatically and would have considerable impact on the prevention of serious lead poisoning and its neurobehavioral effects. Most importantly, universal screening may become a feasible goal.

Many different methods have been used to detect lead in biological matrices such as bodily fluids. Such techniques include: atomic absorption spectrometry, neutron activation analysis, spark source mass spectroscopy, X-ray fluorescence, proton-induced X-ray emission, inductively coupled plasma atomic emission spectroscopy, isotope dilution mass spectrometry, anodic stripping voltammetry (ASV), and differential pulse ASV.

Reeder et al. disclose an ASV detection method coupled with an electrochemical sensor by screen-printing techniques to detect lead in the $10^{-6}$ to $10^{-9}$ M concentration range. See Reeder et al., Sensors and Actuators B, Vol. 52, pp. 58–64 (1998). Also, an electrochemical analyzer coupled to screen-printed disposable sensors for the field screening of trace lead is disclosed by Yarnitzky et al. to detect lead levels of 20–300 μg/L in drinking water (low ionic strength). See Yarnitzky et al., Talanta, Vol. 51, pp. 333–38 (2000).

Furthermore, Yu et al. disclose a lead sensor made by first derivatizing the $Pb^{2+}$ with sodium tetraethylborate to form tetraethyllead, which is then extracted from the headspace over the sample by solid-phase microextraction gas chromatography. See Yu et al., Anal. Chem., Vol. 71, pp. 2998–3002 (1999). The limit of detection for the Yu et al. disclosure was 5–10 ppb for urine and blood samples.

Also, de la Riva et al. disclose a flow-injection system which utilizes room temperature phosphorescent quinolinesulphonic acid lead chelates immobilized on an anion exchange resin to detect lead in seawater and the ng/mL level. See de la Riva et al., Anal. Chim. Acta, Vol. 395, pp. 1–9 (1999). These methods are both costly and time consuming.

None of the above-described prior art, however, discloses an effective method to detect chemical species, such as $Pb^{2+}$ in bodily fluids and other high ionic strength solutions which is time efficient and cost-effective as does the present method.

SUMMARY OF THE INVENTION

An object of the present invention is to provide a method for using sensor devices composed of polymerized crystalline colloidal array (PCCA) materials to detect the presence of certain chemical species in high ionic strength solutions. The process of chemical sensing by the polymerized crystalline colloidal arrays previously disclosed in U.S. Pat. No. 6,187,599 of Asher et al. results from changes in volume of the hydrogel in which the crystalline colloidal array is embedded. This volume change results from immobilization of charge on the hydrogel due to the presence of a chemical species, and causes shifts in the wavelength of light diffracted by the crystalline colloidal array, wherein such a wavelength change is sensed by the color change.

However, high ionic strength solutions decrease the magnitude of the hydrogel volume change, which results from charge immobilization by the sensor. Thus, the present invention is directed to a method for removing much of the interference caused by high ionic strength solutions.

An object of the present invention is to first equilibrate the sensor (composed of the polymerized crystalline colloidal array) in the solution containing the specific chemical species, and subsequently place the sensor into a low ionic strength solution, such as, but not limited to, water. As a result of this step of placing the sensor in the low ionic solution strength, the ionic compounds giving rise to the high ionic strength solution diffuse out of the hydrogel, while the bound chemical species are retarded in the PCCA material and a transient swelling of the hydrogel occurs. The magnitude of this transient swelling is proportional to the chemical species concentration.

Therefore, a further object of the present invention is to provide a method whereby a transient response of sensor materials (composed of a polymerized crystalline colloidal array) is used to detect the concentration of certain chemical species in high ionic strength solutions.

Still another object of the present invention is to provide an optrode for use in high ionic strength solutions, wherein the optrode comprises the polymerized crystalline colloidal array and an optical fiber assembly which illuminates the polymerized crystalline colloidal array, collects the back-diffracted light, and images it to a spectrometer for analysis.

One skilled in the art will appreciate that the various embodiments disclosed herein, as well as other embodiments within the scope of the invention, will have numerous applications in the environmental, medical and chemical fields.

BRIEF DESCRIPTION OF THE DRAWINGS

The present invention may be better understood with reference to the attached drawings of which

DETAILED DESCRIPTION OF THE INVENTION

The present invention is directed to a method for using sensor devices composed of polymerized crystalline colloidal array (PCCA) materials to detect the presence of certain chemical species in high ionic strength solutions. The overall process of chemical sensing by the PCCA materials was previously disclosed in U.S. Pat. No. 6,187,599 to Asher et al. However, the present method involves the sensor materials undergoing a transient response to detect chemical species in high ionic strength solutions.

The method disclosed herein employs the PCCA chemical sensing materials and endeavors to remove much of the interference associated with high ionic strength solutions. First, the PCCA chemical sensor is equilibrated with the solution containing the chemical species of interest, and diffraction spectra measurements are taken. Subsequently, the PCCA hydrogel is placed in a low ionic strength solution. The ionic compounds that caused the solution to have a high ionic strength (for example, salts in the solution) diffuse out of the hydrogel, while the diffusion of the bound or immobilized chemical species is retarded due to binding by the molecular recognition element. This retardation of the bound chemical species causes a transient swelling of the hydrogel, and the magnitude of this transient swelling is proportional to the concentration of the chemical species.

Figure 1:
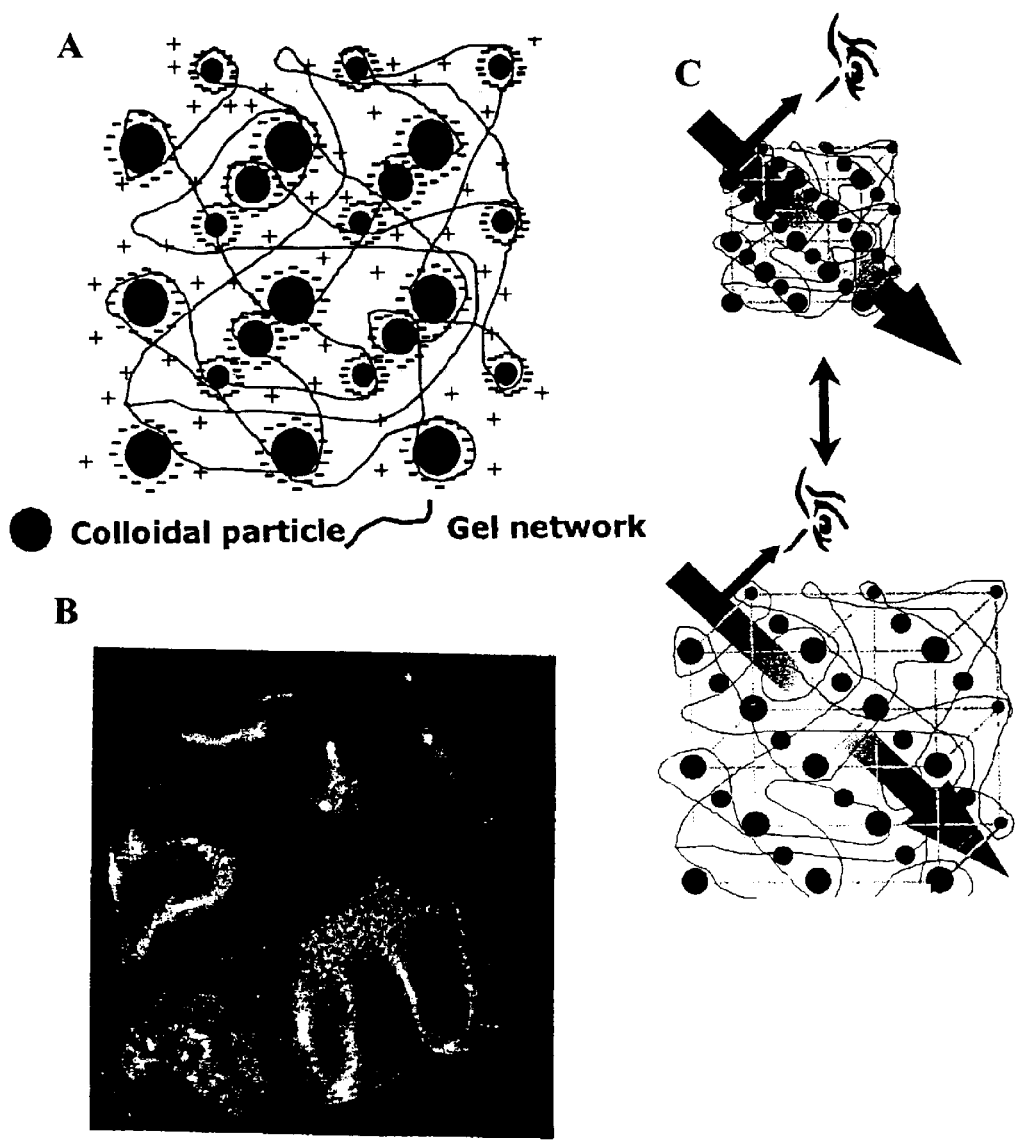
FIG. 1: (A) Body centered cubic polymerized crystalline colloidal array of colloidal particles; (B) Photograph of polymerized crystalline colloidal array; and (C) Diagram showing dependence of diffraction on PCCA volume in that as the PCCA swells, the diffraction red shifts.

The PCCA materials used herein comprise a mesoscopically periodic array of colloidal particles polymerized into a hydrogel. These PCCA materials are shown in FIGS. 1(A) and (B). The array contained in the hydrogel diffracts light in the visible spectral region due to the periodic spacing of the colloidal particles as seen in FIG. 1(C).

The PCCA materials contain molecular recognition components designed to recognize the chemical species of interest and bind those chemical species. Thus, the combination of an array or dispersion of colloidal particles embedded in a hydrogel with a molecular recognition agent forms an effective chemical sensing material and allows for a simple and inexpensive method for detecting chemical species in high ionic strength solutions such as bodily fluids or environmental solutions such as ground water, waste storage, or the like.

As previously mentioned, high ionic strength solutions alone decrease the magnitude of the volume change of the hydrogel because of the immobilization of charge due to the binding of analyte. This interferes with the detection of the small amount of charge due to chemical species immobilized by the sensor. Thus, the present invention is directed to a method for removing much of the interference caused by high ionic strength solutions.

Because PCCA materials contain more than 80% water, ionic compounds are free to rapidly diffuse into the PCCA, with diffusion constants similar to the chemical species of interest diffusion constants in pure water. Thus, the PCCA materials show the rich phase transition phenomena typical of hydrogels, since rapid diffusion of the chemical species and resulting volume changes are so prominent in such hydrogels.

The volume of the PCCA hydrogel depends upon three main factors: the free energy of mixing; the elastic free energy; and electrostatic interactions, such as the formation of a Donnan potential due to the presence of immobilized ions. The total free energy of an PCCA hydrogel is represented in Formula I:

$$\Delta G_{tot} = \Delta G_{mix} + \Delta G_{elas} + \Delta G_{elec} \quad (I)$$

The Donnan potential, due to the presence of immobilized ions (for example, the presence of $Pb^{2+}$ attached to a molecular recognition component such as a crown ether), results in an osmotic pressure, which causes the hydrogel to swell against the elastic gel restoring force. The resulting change in the particle array lattice constant operates to shift the wavelength of light diffracted by the hydrogel. This phenomenon is illustrated in FIG. 1(C). Thus, the shift in diffracted wavelength serves as an indication of the identity and the concentration of the target chemical species, for example $Pb^{2+}$.

In a preferred embodiment, the PCCA materials are detecting the presence of $Pb^{2+}$ in bodily fluids or other high ionic strength solutions. The molecular recognition agent or chelating agent employed for binding the $Pb^{2+}$ is a crown ether, which selectively attaches the $Pb^{2+}$ to the hydrogel. When using a PCCA hydrogel to detect $Pb^{2+}$, the response of the PCCA to the presence of $Pb^{2+}$ results from the formation of an osmotic pressure in the hydrogel due to the immobilization of the $Pb^{2+}$ cation within the crown ether. In low ionic strength solutions, this immobilization of the $Pb^{2+}$ cation causes a Donnan potential, which causes the osmotic pressure that swells the hydrogel. However, in high ionic strength solutions (such as bodily fluids, which usually have salt concentrations of greater than 150 mM), the Donnan potential created is attenuated, and decreased swelling is observed. Thus, the sensitivity of the PCCA to $Pb^{2+}$ is decreased.

Figure 8:
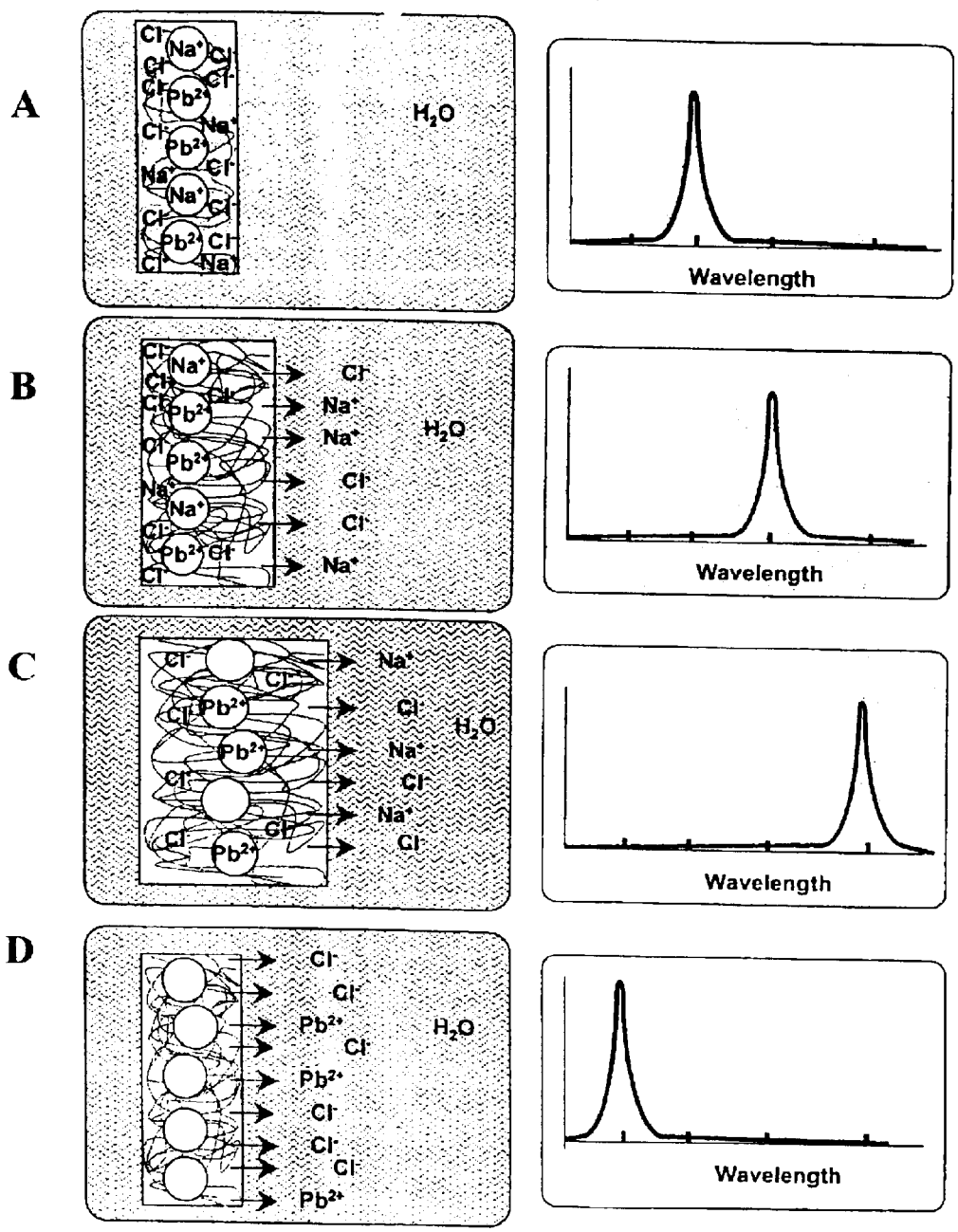
FIGS. 8(A), (B), (C) and (D): Diagram indicating the mechanism of PCCA transient response upon exposure to pure water.

Although, as evidenced in the method of the present invention, chemical sensing in high ionic strength solutions can be achieved. In a particular embodiment, shown in FIG. 8, such chemical sensing may be achieved by incubating the PCCA sensor in a 100 mM NaCl solution containing $Pb^{2+}$, which results in the binding of the $Pb^{2+}$ to the crown ether (FIG. 8(A)). Possibly the $Na^+$ ions compete with the $Pb^{2+}$ to bind to the crown ether because of the high salt concentration, but this competing $Na^+$ binding is not as significant as the $Pb^{2+}$ binding to the crown ether. Because very little osmotic pressure is induced in the hydrogel by $Pb^{2+}$ binding in this incubated solution (because of the high ionic strength of the solution), very little PCCA diffraction shift occurs at this point.

However, after equilibration with the high ionic strength solution, the PCCA is placed in a low ionic strength solution (for example, pure water or other pure low ionic strength solvents in which the hydrogel will respond, such as dimethyl sulfoxide (DMSO) or mixtures of DMSO and water), which is an important step of the present invention. Because the PCCA itself is approximately 80% water, the ions diffuse out of the PCCA hydrogel, with diffusion constants similar to those in pure water (FIGS. 8(B) and (C)). As the ionic strength decreases, the PCCA hydrogel swells proportionally to the amount of cations that are bound. As time progresses, the diffusion of the $Pb^{2+}$, which is bound most strongly, is retarded compared to the diffusion of the other non-bound ions, such as the $Na^+$ ions, and a transient PCCA swelling occurs, causing a transient diffraction red shift (FIG. 8(C)). This transient red shift is followed by a diffraction blue shift as the $Pb^{2+}$ finally diffuses out of the PCCA (FIG. 8(D)).

In embodiments involving the detection of $Pb^{2+}$, high concentrations of $Pb^{2+}$ produce transient wavelength responses that are visible to the human eye, while lower concentrations of $Pb^{2+}$ produce transient wavelength responses that require the use of a spectrophotometer for detection.

The present invention is also useful for detecting other chemical species in high ionic strength solutions. For example, the present invention may detect, inter alia, other ions, cholesterol, glucose, drugs, poisons, DNA sequences, cancer cells, specific proteins, antibodies, bacteria, and viruses. To detect other chemical species according to the present invention, the skilled artisan would appreciate that a molecular recognition component capable of recognizing a chemical species of interest could be attached to a PCCA material in accordance with the present invention. For example, to detect DNA, the compliment to the DNA strand may be used as the molecular recognition component. Similarly, to use the PCCA material to detect glucose, glucose oxidase may be used as the molecular recognition component, and to detect a specific antibody, the antigen that binds to that antibody can be attached to the PCCA.

The present invention is also directed to an optrode for near and remote detection of a chemical species wherein the optrode comprises the PCCA material and an optical fiber assembly which illuminates the PCCA, collects the back diffracted light, and images it to a spectrometer for analysis. The optrode of the present invention includes the PCCA sensing material, which may be attached to a membrane or solid support. The support/PCCA assembly may then be attached to the end of the fiber optic, such that it can be dipped into a sample solution.

When used according to the present invention, the optrode is first dipped into the sample solution for equilibration. Subsequently, the optrode is removed, and a button is pressed which squirts a low ionic strength solution, such as water, at the sensing material in order to wash out the high ionic strength interfering ionic compounds. The transient response is monitored in real time by the fiber optic assembly and spectrometer. The transient wavelength shift is analyzed to determine the chemical species concentration in the solution.

When preparing the PCCA chemical sensing material used according to the present invention, the hydrogel monomer component of the PCCA hydrogels can be any compound that forms a hydrogel which undergoes a volume change in response to a stimulus or stimuli. Examples of suitable gels include, but are not limited to, acrylamide gels, purified agarose gels, N-vinylpyrolidone gels and methacrylate gels. In certain preferred embodiments of the present invention, the hydrogel monomer component used is acrylamide (AMD).

As discussed earlier, the phase transition properties of the hydrogel are modified by functionalizing the hydrogel with a molecular recognition component that specifically binds a chemical species of interest. Any monomer having molecular recognition capabilities for the desired chemical species can be used. For example, 4-acryloylamidobenzo 18-crown-6 ether, which preferably binds $Pb^{2+}$ ions, can be used if $Pb^{2+}$ is the chemical species of interest. Other crown ethers, cyclodextrans, calixarenes, and other chelating agents may also be used as the molecular recognition component. Furthermore, complimentary DNA strands, glucose oxidase, or specific antigens may be used as the molecular recognition component as previously described.

Any suitable colloidal particles can be used in preparing the crystalline colloidal array disclosed herein. For example, the particles can be colloidal polystyrene, polymethylmethacrylate, silicon dioxide, aluminum oxide, polytetrafluoroethylene or any other suitable materials, which are generally uniform in size and surface charge. Colloidal polystyrene is used in certain preferred embodiments. The particles are chosen depending upon the optimum degree of ordering and the resulting lattice spacing desired for the particular application. The particles preferably have a diameter between about 50 and 1000 nanometers and may be either synthesized as discussed below or obtained commercially. Colloidal particles that can be used in accordance with this embodiment have been described by Reese et al., 2000, *Journal of Colloid and Interface Science* 232: 76–80, incorporated herein by reference.

Monodisperse colloids can be prepared by emulsion polymerization or any other means. For example, an emulsion polymer colloid can be prepared by mixing the desired monomer with a cross-linking agent, a surfactant to aid in the formation of the emulsion, a buffer to keep the pH of the solution constant and to prevent particle coagulation, and a free-radical initiator to initiate polymerization. Various compounds can be used to prepare the emulsion polymer colloid, so long as compatibility problems do not arise. The particles should then be purified by the use of centrifugation and/or dialysis, followed by shaking with ion exchange resin.

Following polymerization, the particles may be stored in an ion exchange resin, such as a bath of 10% by weight suspension of ion exchange resin such as analytical grade AG501-X8 mixed bed resin commercially available from Bio-Rad of Richmond, Calif. The ion exchange resin should preferably be cleaned prior to use through a suitable procedure such as that of Vanderhoff et al., 1968, *Journal of Colloid and Interface Science*, 28, 336–337, incorporated herein by reference.

The electrically charged particles are then allowed to self assemble to form a crystalline colloidal array. This assembly takes place in a suitable solvent, preferably water. A hydrogel monomer, a molecular recognition component, a cross-linking agent and a polymerization initiator are then added to the crystalline colloidal array. Any suitable initiator can be used, such as a thermal initiator or a photoinitiator. Preferably, a UV photoinitiator is used. A preferred UV photoinitiator for this use is 2,2'-diethoxyacetophenone. Any cross-linking agent, gel monomer and molecular recognition component discussed above can be used.

After formation, the mixture is then polymerized. Any means known in the art can be used to initiate polymerization, so long as the method for polymerization does not destroy or otherwise disorder the crystalline colloidal array. Preferably, the polymerization is accomplished by placing the mixture between two plates, preferably quartz plates separated by a parafilm spacer, at room temperature. The plates are then exposed to UV light. Exposure to the UV light effects complete polymerization after about 5 minutes. Upon completion of the polymerization, the plates are removed and a stable polymerized crystalline colloidal array (PCCA) results. This film can be approximately 125 microns thick and can be made thinner or thicker based upon the needs of the user.

The following examples are intended to illustrate the invention and should not be construed as limiting the invention in any way.

EXAMPLES

Example 1

PCCA Formation

The $Pb^{2+}$ sensing polymerized crystalline colloidal array used in this Example was formed according to the methods disclosed in Holtz et al., Nature, Vol. 389, pp. 829–32 (1997), Holtz et al., Anal. Chem., Vol. 70, pp. 780–91 (1998), and U.S. Pat. Nos. 5,854,078 and 5,898,004 to Asher et al., and the specifications of these references are incorporated herein by reference in its entirety. In the PCCA formation of the present Example, however, a hydrophobic coating (specifically an organopolisyloxane solution commercially available as Sigmacote from Sigma Chemical Co., St. Louis, Mo.) was used to coat the quartz plates in order to aid release of the PCCA after polymerization.

The monodisperse polystyrene particles used to form the PCCA were synthesized according to the procedure described in Reese et al., J. Coll. Int. Sci., Vol. 232, pp. 76–80 (2000), which is incorporated herein by reference in its entirety. The monodisperse polystyrene particles used were highly charged and were approximately 120 nm in diameter.

PCCA samples were made with two different compositions. PCCA "A" was made according to the procedure disclosed by Holtz et al., Anal. Chem., Vol. 70, pp. 780–91 (1998) except that the concentration of crown ether was doubled. Specifically, a mixture of 103 mg acrylamide (AMD), 7.9 mg methylene bis-acrylamide (BIS) and 56 mg 4-acryloylamidobenzo-18-crown-6 in 160 mg of water was added to 1.96 g of a 93 mg/mL dispersion of 120 nm monodisperse polystyrene colloidal particles. (The AMD and BIS are commercially available from Fluka, and the 4-acryloylamidobenzo-18-crown-6 is commercially available from Acros Organics/Fisher Scientific in Pittsburgh, Pa.)

An ion-exchange resin (commercially available as Bio-Rad, AG501-X8) and two drops of 2,2-diethoxyacetophenone (DEAP, a UV photoinitiator, commercially available from Acros Organics/Fisher Scientific) were added, and the solution was gently shaken. The solution was subsequently centrifuged, and the supernatant was injected into a chamber formed by two quartz cell flats separated by a 125 $\mu$m spacer. This cell was illuminated with ultraviolet light, after which the cell was opened to release the PCCA film, which was washed overnight in water.

The second composition, PCCA "C", was formed analogously to PCCA "A" described above, except that additional crown ether (84 mg) was incorporated into PCCA "C", while less methylene bis-acrylamide (BIS) (3.95 mg) was used in this formation.

Figure 2:
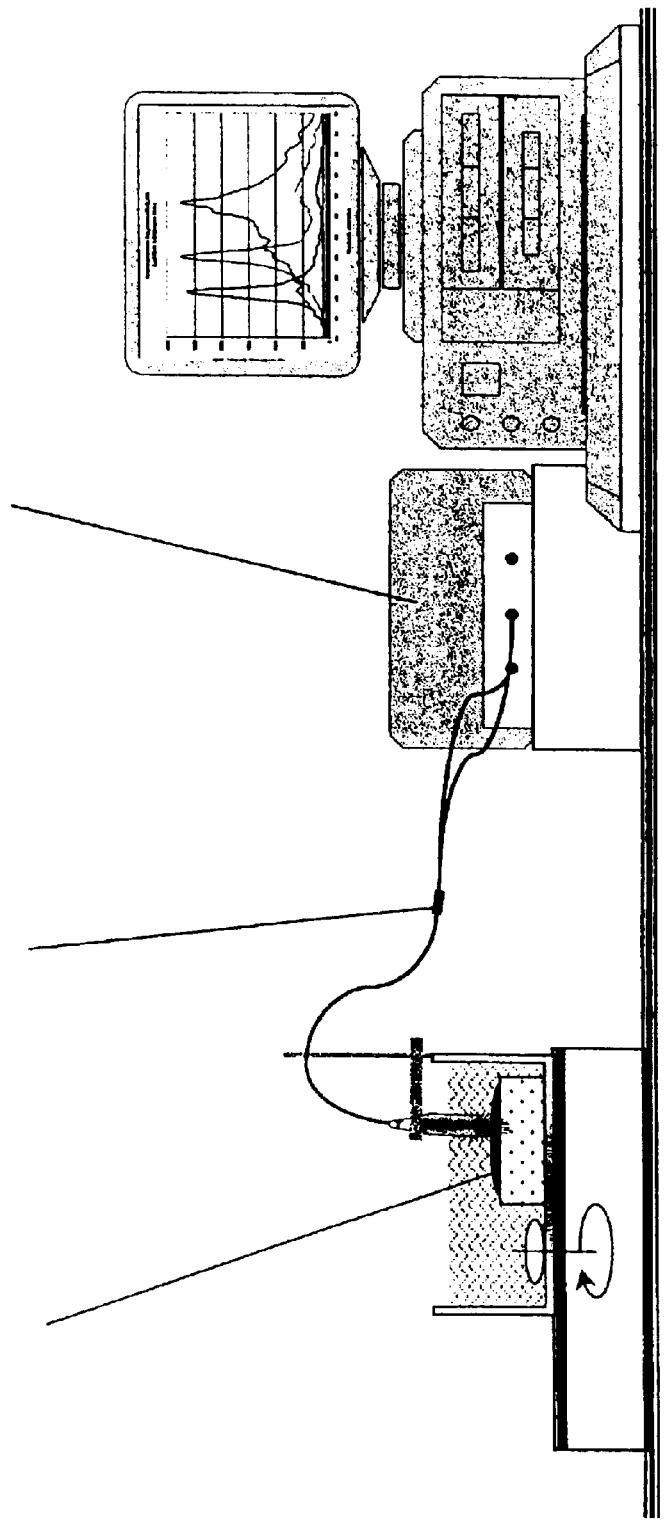
FIG. 2: Schematic diagram of equipment for diffraction measurement showing a PCCA attached to the quartz plate in a stirring solution reservoir and a CCD spectrometer.

FIG. 2 shows a CCD Array Spectrophotometer (Model 400, commercially available from Spectral Instruments, Inc. in Tucson, Ariz.) equipped with a bifurcated fiber-optic dip probe that was used to obtain the diffraction intensity measurements from the PCCA. Transmission measurements were obtained by using an absorption spectrophotometer (commercially available as the Perkin Elmer Lambda 9).

As seen in FIG. 2, the PCCA, attached to a quartz plate, was immersed in a stirred solution. A 9 around 1 fiber optic probe was immersed in the solution and illuminated the surface of the PCCA. The diffracted light was measured at ~180° backscattering, thus it was collected by the central large fiber at approximately normal incidence. The analyte and washing solutions were gently replaced between measurements.

Example 2

PCCA "A" $Pb^{2+}$ Detection

Once PCCA "A" was formed and placed into the sampling configuration shown in FIG. 2, diffraction measurements were taken for PCCA "A" in pure water. The diffraction from the 111 plane of the PCCA crystal was measured in backscattering.

Figure 3:
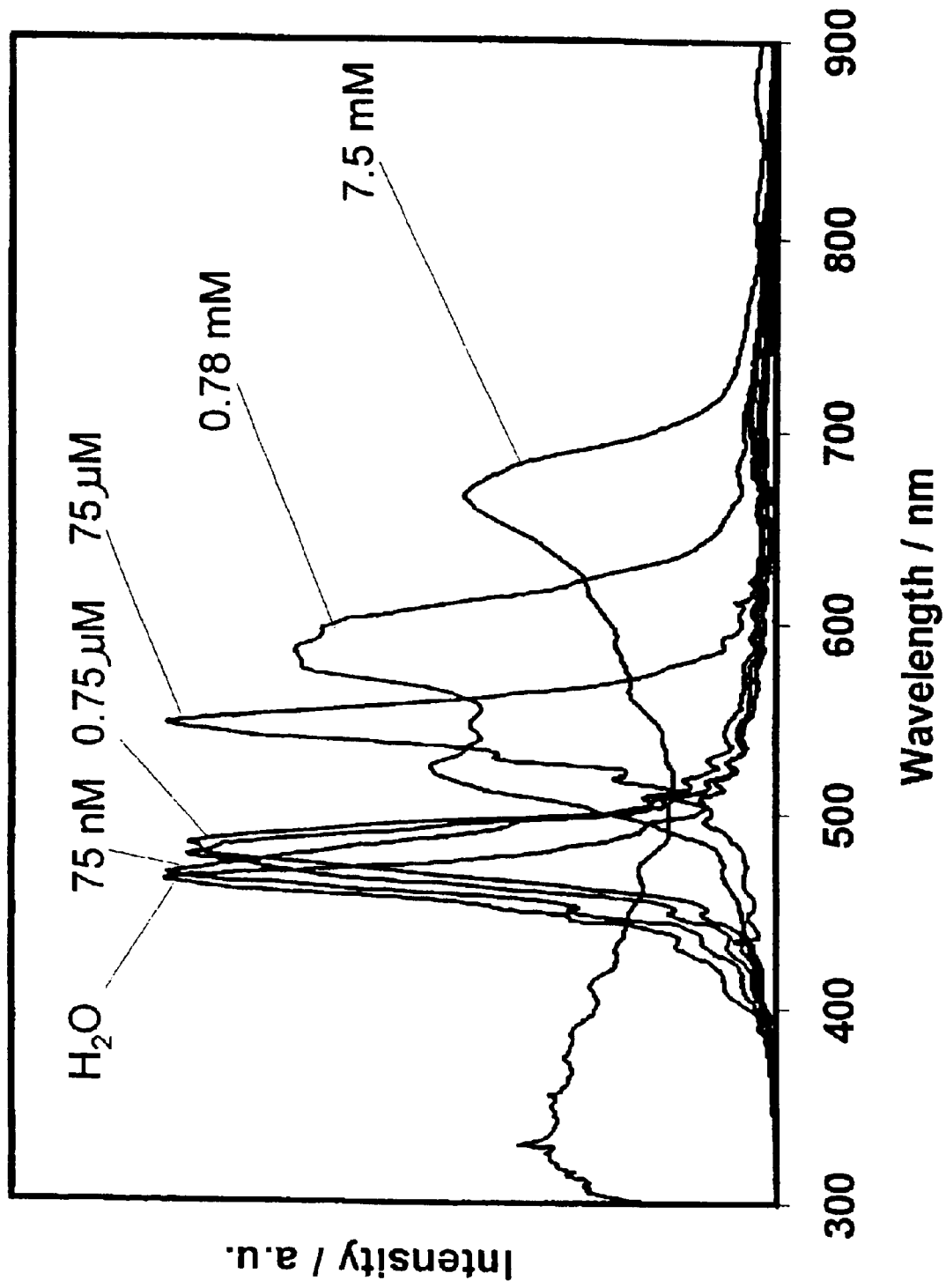
FIG. 3: Diffraction spectrum for a PCCA in pure water, showing the dependence of the spectra on $Pb^{2+}$ concentration.

Subsequently, PCCA "A" was exposed to a series of solutions containing $Pb^{2+}$, and FIG. 3 shows the dependence of the diffraction spectra of PCCA "A" at concentrations of $Pb^{2+}$ between zero and 7.5 mM. The diffraction peak monotonically red shifted from the original sharp peak at 466 nm in pure water (where $Pb^{2+}$ was absent) to 667 nm as the $Pb^{2+}$ concentration was increased to 7.5 mM $Pb^{2+}$, with a broad second order diffraction peak appearing at ~330 nm. Note that at Pb concentrations above 0.78 $\mu$M, the diffraction band appears as a doublet.

As seen in FIG. 3, the red shift saturates at high $Pb^{2+}$ concentrations, as was previously observed by Holtz et al., Nature, Vol. 389, pp. 829–32 (1997), Holtz et al., Anal. Chem., Vol. 70, pp. 780–91 (1998), and U.S. Pat. Nos. 5,854,078 and 5,898,004 to Asher et al. (all herein incorporated by reference in their entirety). This decreased PCCA swelling at high $Pb^{2+}$ concentrations results from a decrease in the hydrogel's swelling osmotic pressure because of the high ionic strength of the solution. Thus, this Example clearly illustrates the need for a modified method of detecting $Pb^{2+}$ in high ionic strength solutions.

Example 3

PCCA "C" $Pb^{2+}$ Detection

Figure 4:
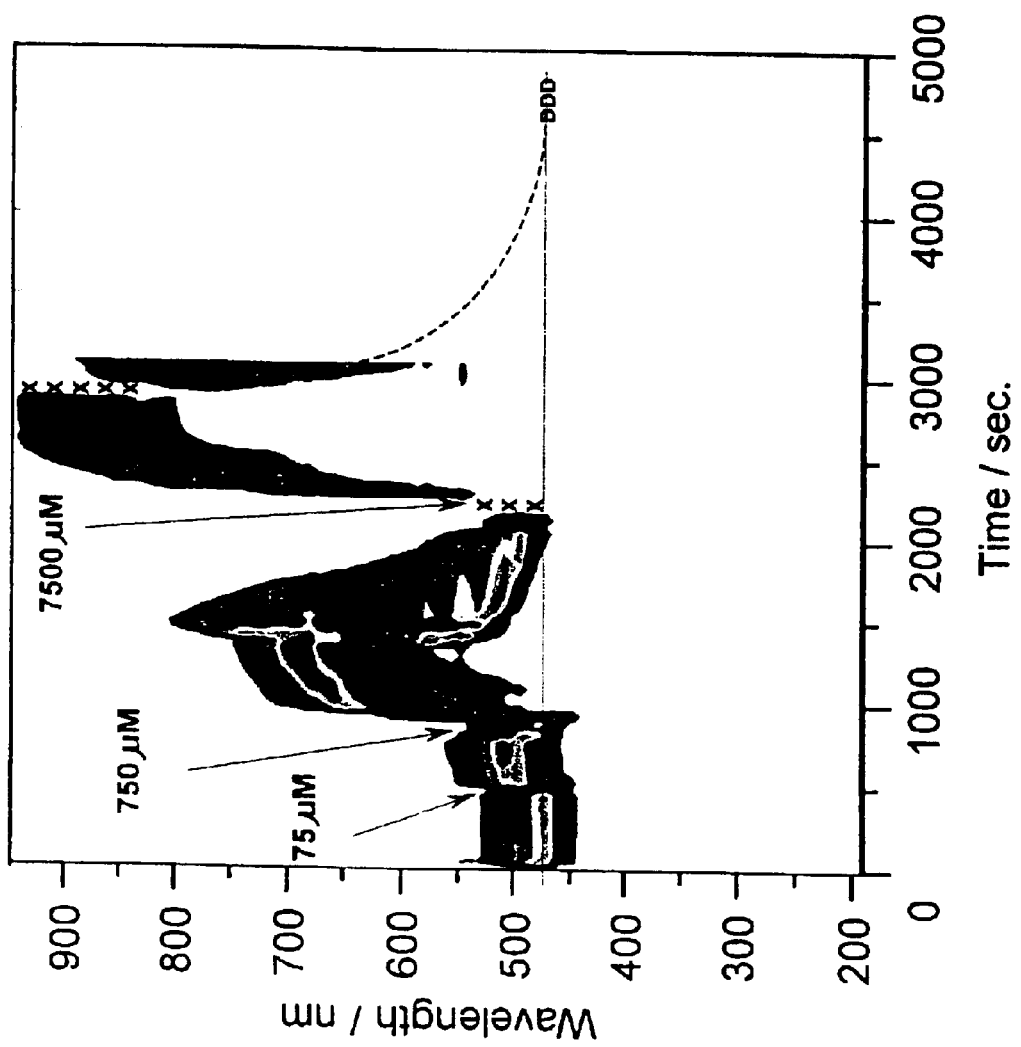
FIG. 4: Plot of time dependence of the response of a PCCA to changes in $Pb^{2+}$ concentration. The areas delineated by "XXX" were missed during the acquisition, and the dashed line indicates the expected time course of the blue shift as the PCCA relaxed in the pure water solution.

Once PCCA "C" was formed, diffraction measurements were taken to study the effectiveness of the PCCA as a chemical sensor for detecting $Pb^{2+}$ concentration. The topological plot shown in FIG. 4 illustrates the time dependence of the response of PCCA "C" to changes in $Pb^{2+}$ concentration. Spectra were measured every 10 seconds. The PCCA was immersed in pure water at t=0, and showed a peak maximum at 472 nm. At t=500 seconds, the water was replaced with a 75 $\mu$M $Pb^{2+}$ solution. The PCCA swelled within 1 minute, and equilibrated within 8 minutes to red shift the diffraction peak from 472 nm to 502 nm. At ~750 seconds, after the PCCA ceased swelling, the 75 $\mu$M $Pb^{2+}$ solution was exchanged with pure water. The PCCA diffraction then blue shifted from 502 nm back to 472 nm. This blue shift was quasi-exponential with a time constant of ~3 minutes.

At t=950 seconds, the water was replaced with a 750 $\mu$M $Pb^{2+}$ solution, and the PCCA diffraction red shifted from 472 nm to 704 nm with a time constant of ~3 minutes. At ~1375 seconds, the 750 $\mu$M $Pb^{2+}$ solution was replaced with pure water, and the diffraction blue shifted back to the original value with a time constant of ~2 minutes. Finally, at ~2250 seconds, the water was replaced with a 7.5 mM $Pb^{2+}$ solution. The PCCA diffraction red shifted from 472 nm to greater than 910 nm. (The sensitivity of the CCD spectrometer used herein is poor at wavelengths greater than 910 nm.) Subsequently, replacement of the 7.5 mM $Pb^{2+}$ solution with pure water returned the diffraction back to 472 nm at ~4500 seconds.

The data observed thus far in this example and reported in FIG. 4 demonstrate that the PCCA response to $Pb^{2+}$ is fully reversible even at relatively high $Pb^{2+}$ concentrations.

Figure 5:
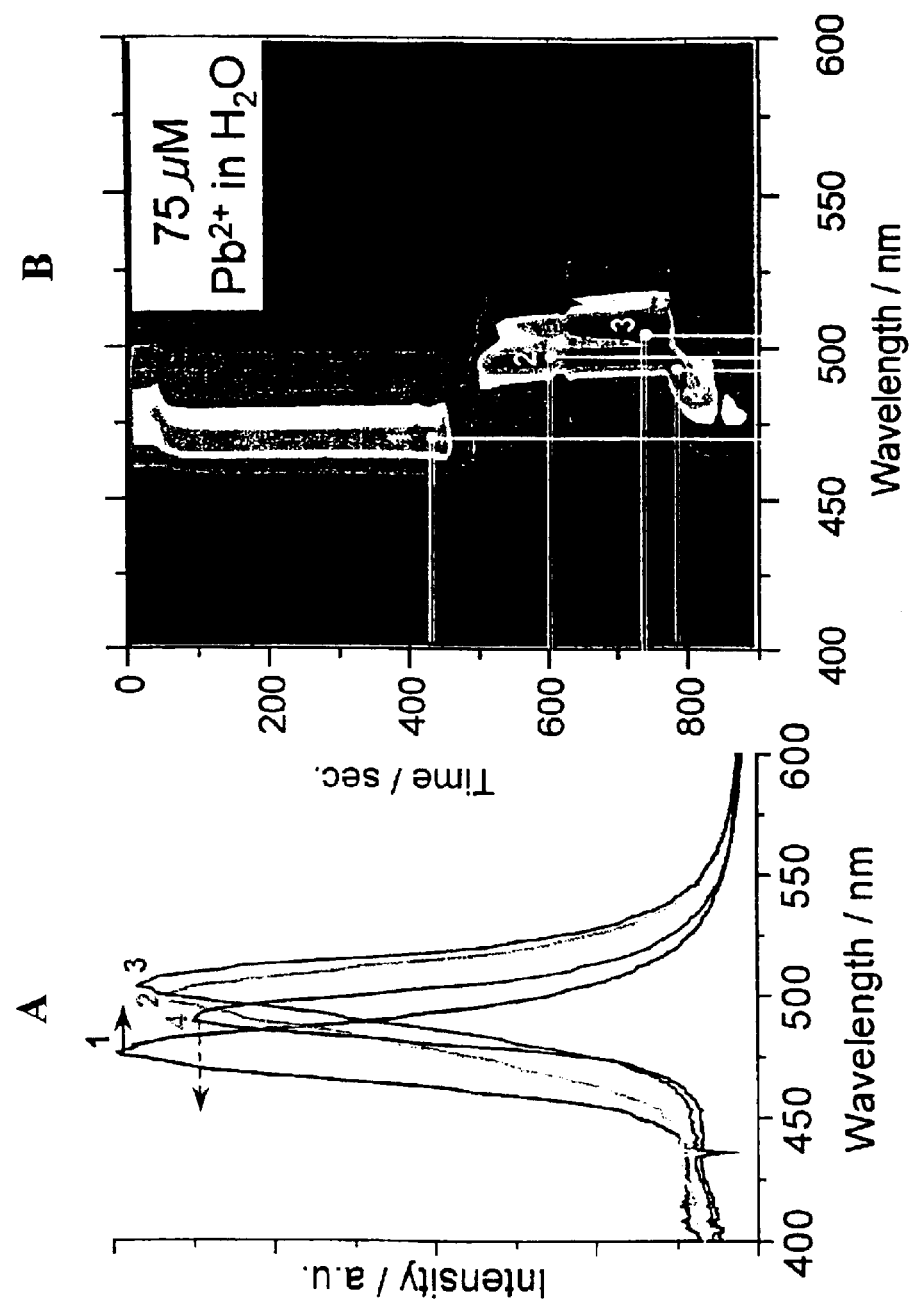
FIGS. 5(A) and (B): Expanded plot and topological view, respectively, of response of PCCA "C" to 75 μM $Pb^{2+}$ concentration (from FIG. 4).

FIGS. 5(A) and (B) (which are expanded views of FIG. 4) show that with the introduction of 75 $\mu$M $Pb^{2+}$, the PCCA's diffraction peaks remain relatively symmetric as the PCCA volume changes and the diffraction red shifts. The diffraction peaks remain relatively symmetric as they blue shift also, due to the replacement of the 75 $\mu$M $Pb^{2+}$ solution with pure water.

Figure 6:
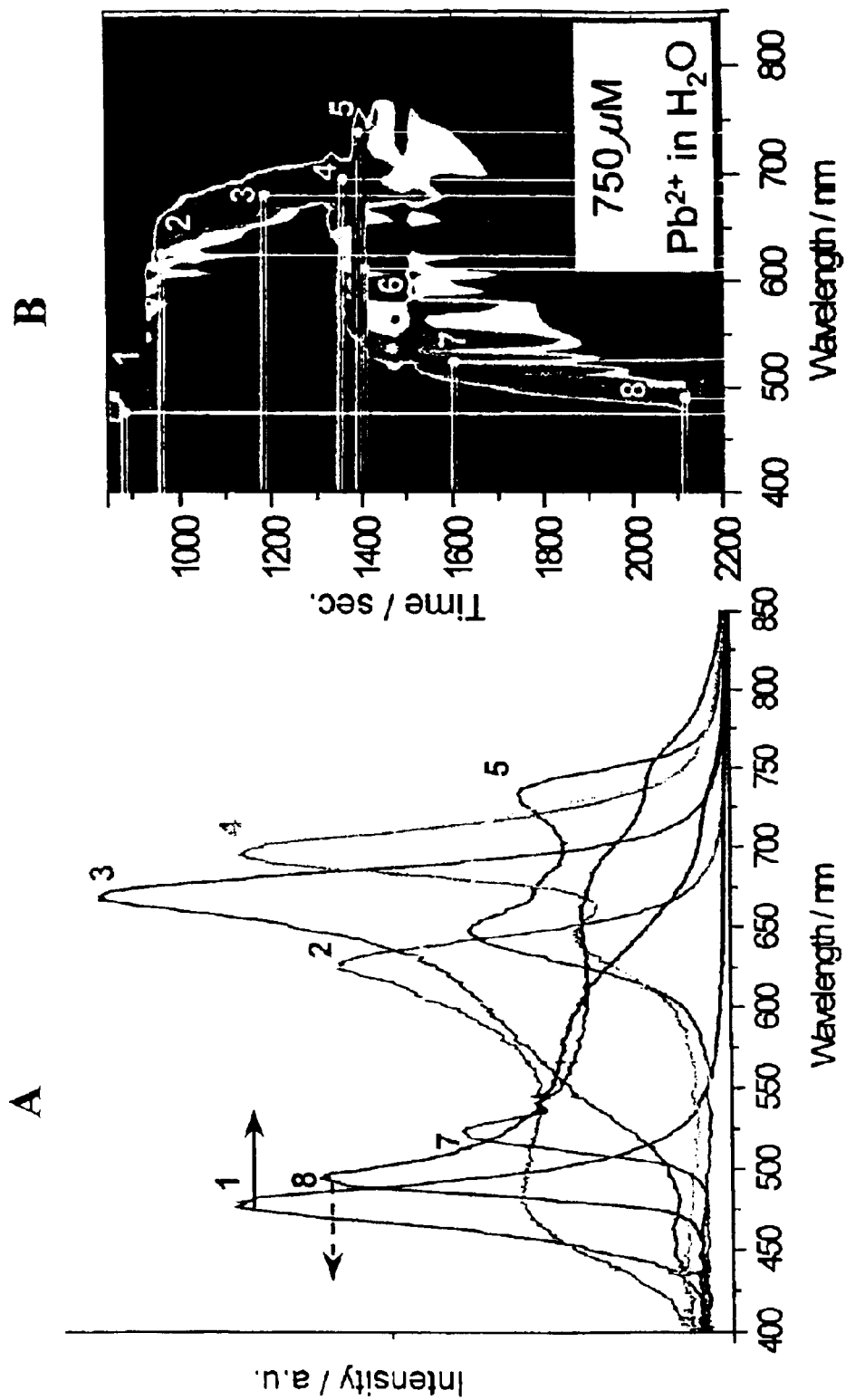
FIGS. 6(A) and (B): Expanded plot and topological view, respectively, of response of PCCA "C" to 750 μM $Pb^{2+}$ concentration (from FIG. 4).

In contrast, FIGS. 6(A) and (B) show that when PCCA "C" responded to the higher 750 μM $Pb^{2+}$ concentration solution, this resulted in peak broadening of the shifted peaks. At this higher $Pb^{2+}$ concentration, a bound $Pb^{2+}$ concentration gradient occurs across the PCCA thickness due to the finite $Pb^{2+}$ diffusion constant. This causes the PCCA layer closest to the analyte solution to swell prior to the swelling of the inner layer. Thus, the diffraction peak shape, which is contributed by the entire PCCA thickness, evolves as $Pb^{2+}$ diffuses into and out of the gel.

Furthermore, FIGS. 6(A) and (B) show a transient red shift of the PCCA's diffraction spectra upon replacement of the 750 μM $Pb^{2+}$ solution with pure water. The 702 nm equilibrium peak maximum for 750 μM $Pb^{2+}$ (peak 4) transiently shifts to a 640 nm and 740 nm doublet (peak 5) upon replacement of the 750 μM $Pb^{2+}$ solution with pure water. This doublet results from the fact that although the addition of pure water exchanges out the bound $Pb^{2+}$, which will ultimately blue shift the PCCA diffraction, the short time behavior results in an PCCA solution ionic strength decrease which red shifts the diffraction. Thus, the transient 740 nm peak is interpreted to be diffraction from an interior segment of PCCA "C" that has a decreased ionic strength, while the 640 nm component of the doublet results from an exterior segment of PCCA "C" where the $Pb^{2+}$ concentration has decreased.

Figure 7:
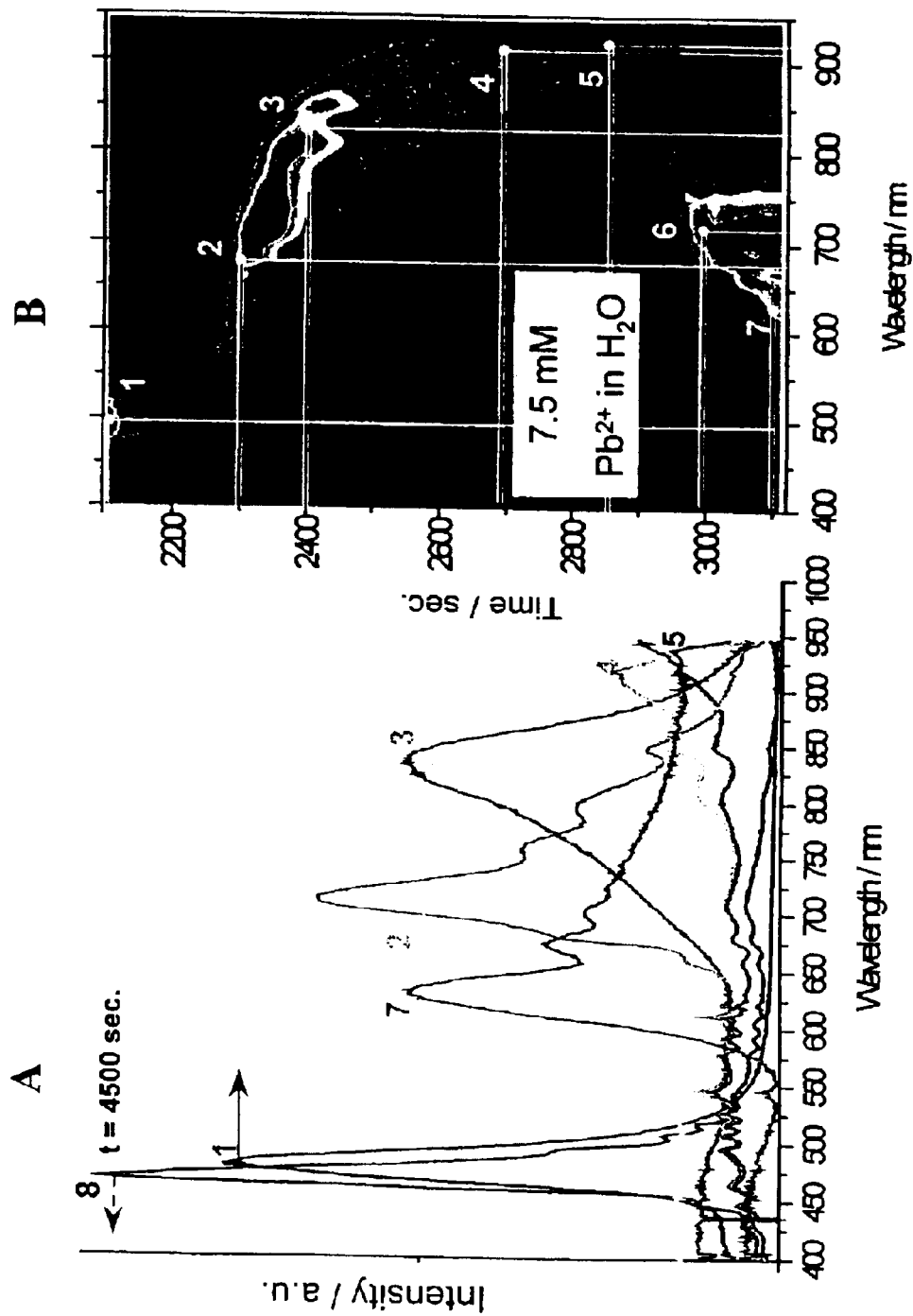
FIGS. 7(A) and (B): Expanded plot and topological view, respectively, of response of PCCA "C" to 7.5 mM $Pb^{2+}$ concentration (from FIG. 4).

In contrast, FIGS. 7(A) and (B) show a much more complicated diffraction peak shifting and broadening in response to immersion of PCCA "C" in 7.5 mM $Pb^{2+}$. The diffraction peak initially red shifts and broadens out past 950 nm, the limit of the spectrometer used herein. After the 7.5 mM $Pb^{2+}$ solution is replaced with pure water, the diffraction blue shifts through a similar set of broadened and skewed peaks to its original symmetric peak at 472 nm (peak 8 shown at t=4500 seconds). Because the spectrometer used herein responds only to wavelengths less than 950 nm, the transient red shift upon replacement with pure water was unable to be characterized.

Example 4

PCCA "C" $Pb^{2+}$ Detection in NaCl Solution

Figure 9:
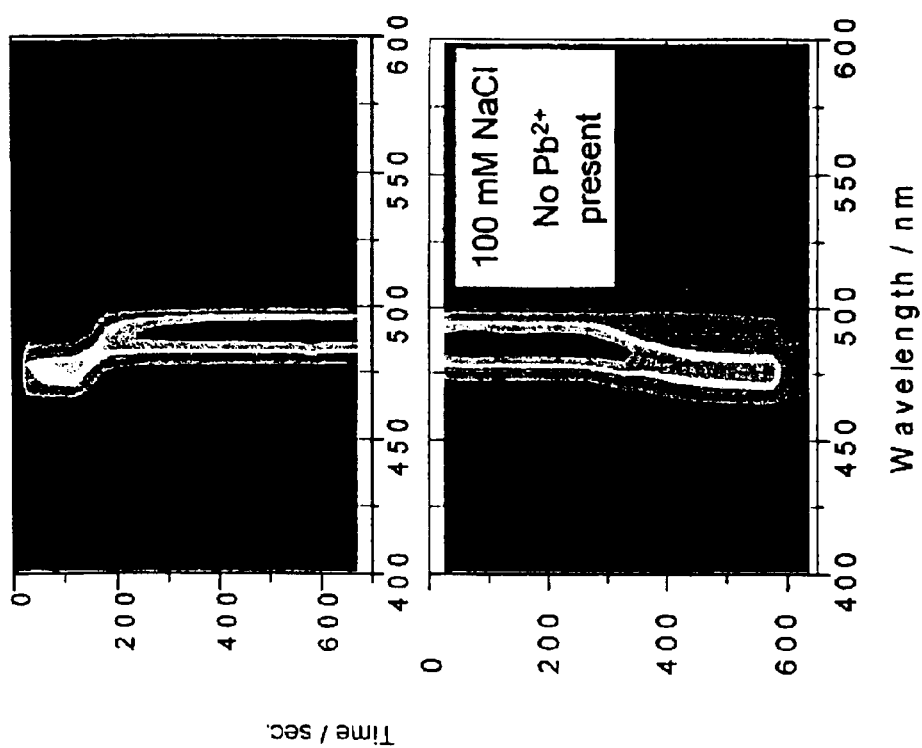
FIG. 9: Topological plot of PCCA "C" response to 100 mM NaCl.

In this Example, PCCA "C" was moved from pure water and equilibrated in a 100 mM NaCl solution, and diffraction spectra measurements of the PCCA's response to the NaCl solution were taken. FIG. 9 shows that the diffraction of PCCA "C" shifts from 475 nm in pure water to a value of 487 nm over a period of 10 minutes after being immersed in the 100 mM NaCl solution. In the 100 mM NaCl solution, the diffraction spectra for PCCA "C" remained at 487 nm indefinitely. (A different section of PCCA "C" showed diffraction at 485 nm in a 100 mM NaCl solution). When the NaCl solution was replaced with pure water, the diffraction blue shifted back to 476 nm, and no transient red shift was observed, presumably due to the small binding affinity of the $Na^+$ to the crown ether.

Figure 10:
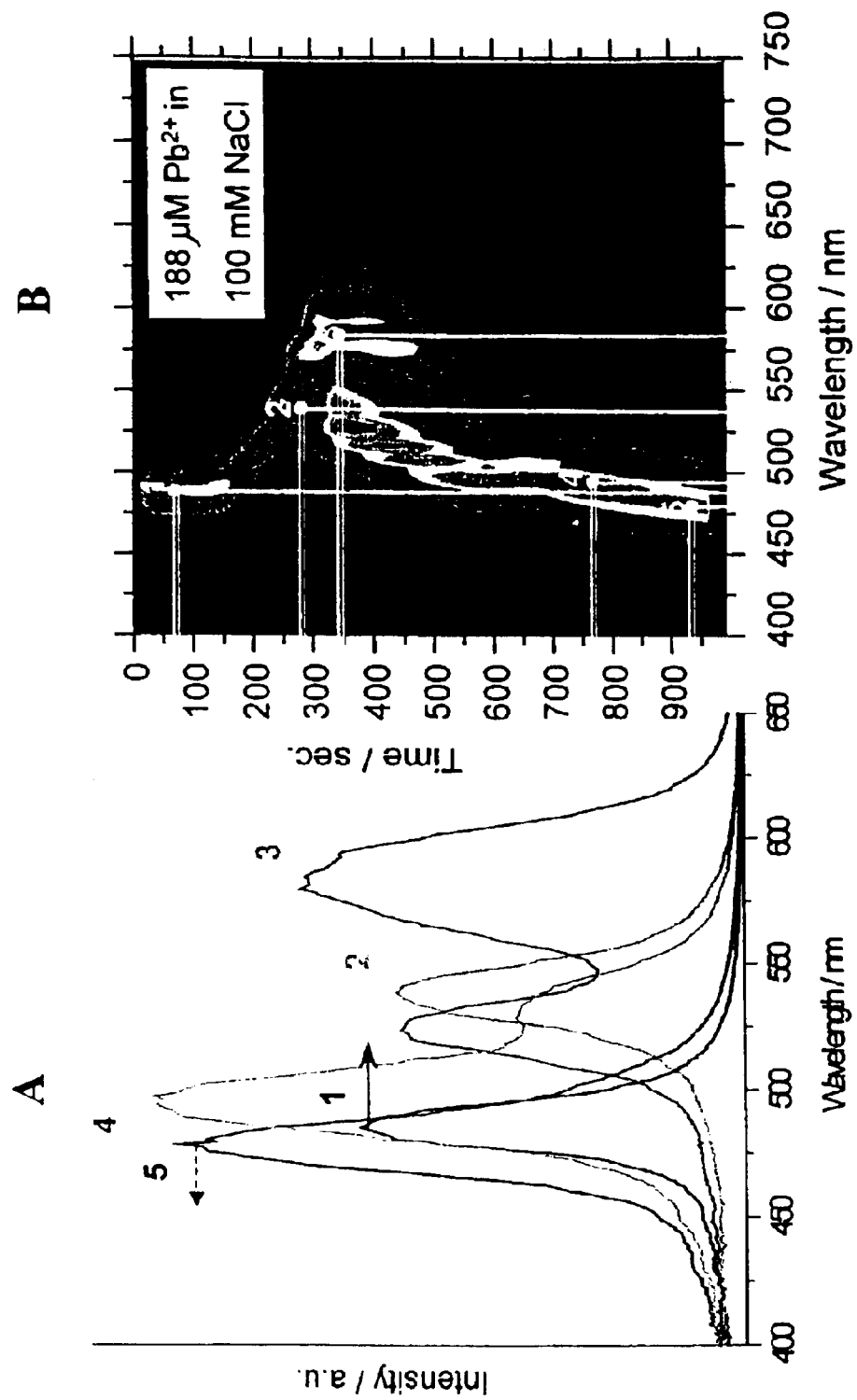
FIGS. 10(A) and (B): Plot and topological view, respectively, of transient response of PCCA "C" in a solution of 188 μM $Pb^{2+}$ in 100 mM NaCl to pure water.

Subsequently, PCCA "C" was placed in solutions containing various concentrations of $Pb^{2+}$, and diffraction spectra were taken. FIGS. 10(A) and (B) show the response of PCCA "C" to a solution of 188 μM $Pb^{2+}$ in 100 mM NaCl. The PCCA diffracts 488 nm light after incubation in the 188 μM $Pb^{2+}$, 100 mM NaCl solution, which is essentially identical to the diffraction in a 100 mM NaCl solution. (FIG. 9 showed a diffraction wavelength of 487 nm in the 100 mM NaCl solution with no $Pb^{2+}$ present.) Thus, the presence of $Pb^{2+}$ does not cause the diffraction of PCCA "C" to red shift.

However, replacement of the 188 μM $Pb^{2+}$, 100 mM NaCl solution with pure water results in a transient diffraction red shift, wherein the maximum diffraction occurs at 580 nm 5 minutes after immersion in pure water (peak 3). This maximum transient response is a diffraction doublet (peak 3, shown at 526 nm and 580 nm in FIG. 10(A)) that is similar to peak 5 previously observed in FIG. 6(A). This doublet is presumably due to an inhomogeneity in the ionic strength and $Pb^{2+}$ concentration along the PCCA thickness. The pure water diffraction returned to 480 nm after 15 minutes.

Figure 11:
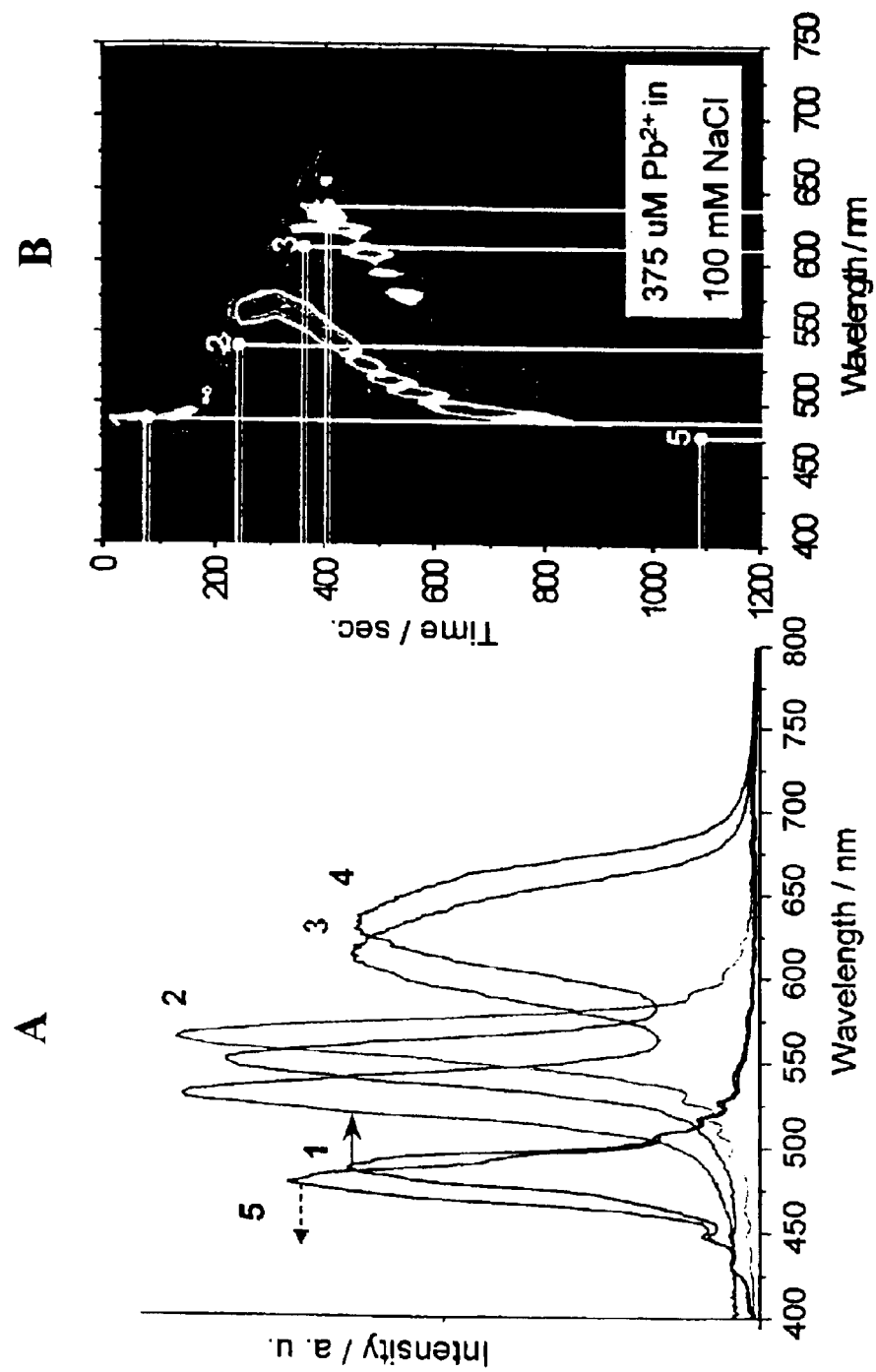
FIGS. 11(A) and (B): Plot and topological view, respectively, of transient response of PCCA "C" in a solution of 375 μM $Pb^{2+}$ in 100 mM NaCl to pure water.

FIGS. 11(A) and (B) show the transient response of PCCA "C" to pure water after incubation in a solution of 375 μM $Pb^{2+}$ in 100 mM NaCl. The diffraction initially occurs at 489 nm in the 375 μM $Pb^{2+}$, 100 mM NaCl solution. After that solution is exchanged with pure water, a much larger transient red shift is observed for this higher concentration $Pb^{2+}$ solution than the previous red shift seen in FIGS. 10(A) and (B). The maximum red shifted diffraction appears as a 548 nm somewhat symmetric peak, and a 630 nm broad, skewed peak doublet (shown as peak 4 in FIG. 11).

Both components of this doublet (the 548 nm peak and the 630 nm peak) are red shifted (by 22 nm and 50 nm, respectively) compared to the doublet (seen at 526 μm and 580 nm) resulting from the lower concentration 188 μM $Pb^{2+}$ in 100 mM NaCl solution. Thus, the magnitude of the transient response is related to the concentration of $Pb^{2+}$ in that the magnitude of the response increases as $Pb^{2+}$ concentration increases, and, therefore, the results obtained in this Example indicate that such transient diffraction responses of PCCA materials can be used to detect $Pb^{2+}$ concentrations in high ionic strength solutions such as bodily fluids.

Example 5

PCCA "C" $Pb^{2+}$ Detection in Fetal Bovine Serum

The response of PCCA "C" to concentrations of $Pb^{2+}$ dissolved in fetal bovine serum was studied next, since fetal bovine serum has salt concentrations similar to those found in blood (140 mM $Na^+$ concentration, for example). The fetal bovine serum used is commercially available from GIBCO/Life Technologies in Grand Island, N.Y.

The highest concentration of fetal bovine serum stock solution was prepared by dissolving a weighed amount of lead nitrate (commercially available from Fluka) in a large volume of fetal bovine serum. The solutions of lower lead nitrate concentrations used herein were obtained by mixing the stock solutions with pure fetal bovine serum. Although $Pb^{2+}$ is known to bind to proteins and other species present in bodily fluids (and this binding would decrease the availability of $Pb^{2+}$ to the crown ether on the PCCA), if $Pb^{2+}$ can exchange between sites, the $Pb^{2+}$ concentrations detected herein will depend upon the relative affinity of the crown ether for $Pb^{2+}$ compared to other chelating molecules found in the fetal bovine serum.

Figure 12:
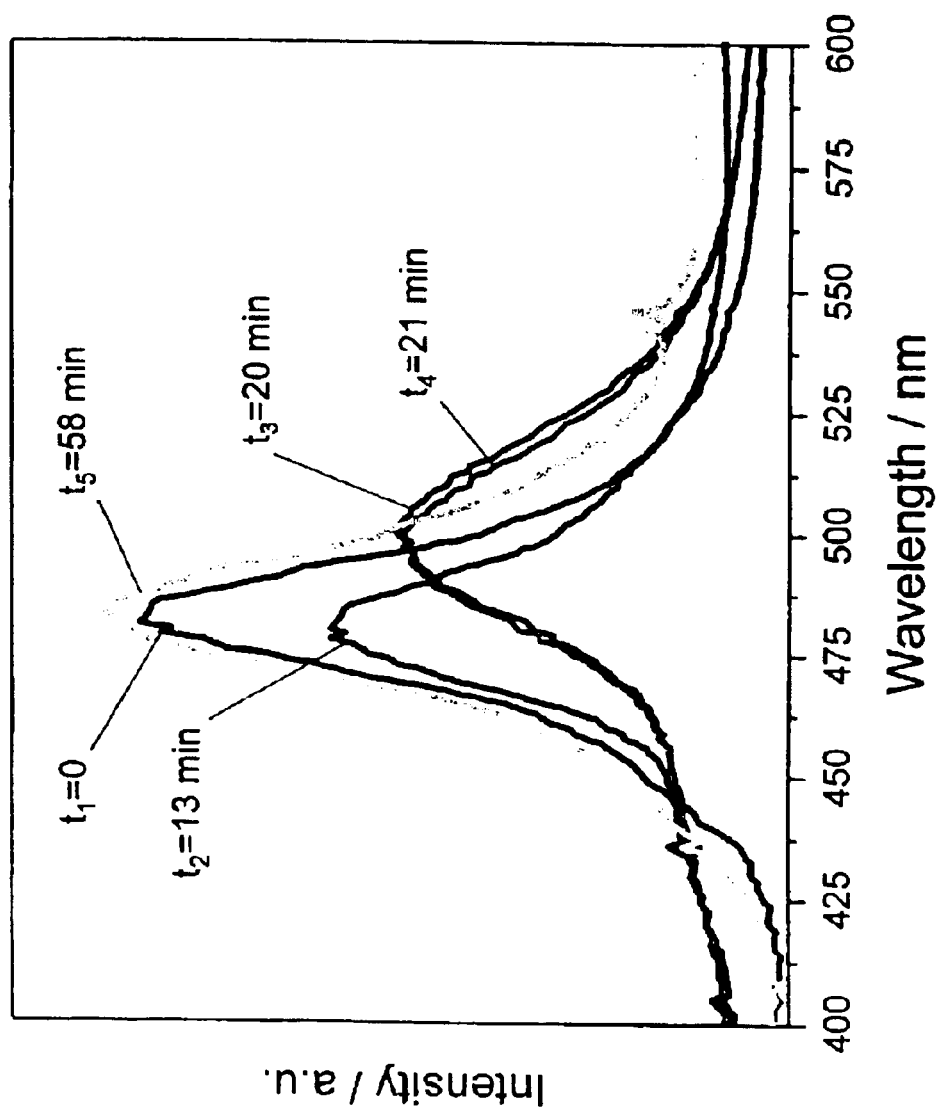
FIG. 12: Diffraction spectra showing response of PCCA "C" incubated in pure fetal bovine serum to pure water.

FIG. 12 shows the transient response of PCCA "C", incubated in pure fetal bovine serum, to immersion in pure water. The PCCA, which diffracted at 481 nm in equilibrium with pure fetal bovine serum, was exposed at t=13 minutes to pure water. The spectrum was measured just after the pure water was placed in contact with the PCCA. Although the maximum of the 481 nm band had not yet shifted, a skew to a longer wavelength was visible. At t=20 minutes, a maximum red shift is observed at 501 nm. The spectra then began to blue shift by t=21 minutes. The diffraction wavelength returned to its value in pure water of 483 nm by t=58 minutes. Thus, pure fetal bovine serum produces a small ~20 nm transient red shift, analogous to that of the 100 mM NaCl solution discussed in previous Examples.

Figure 13:
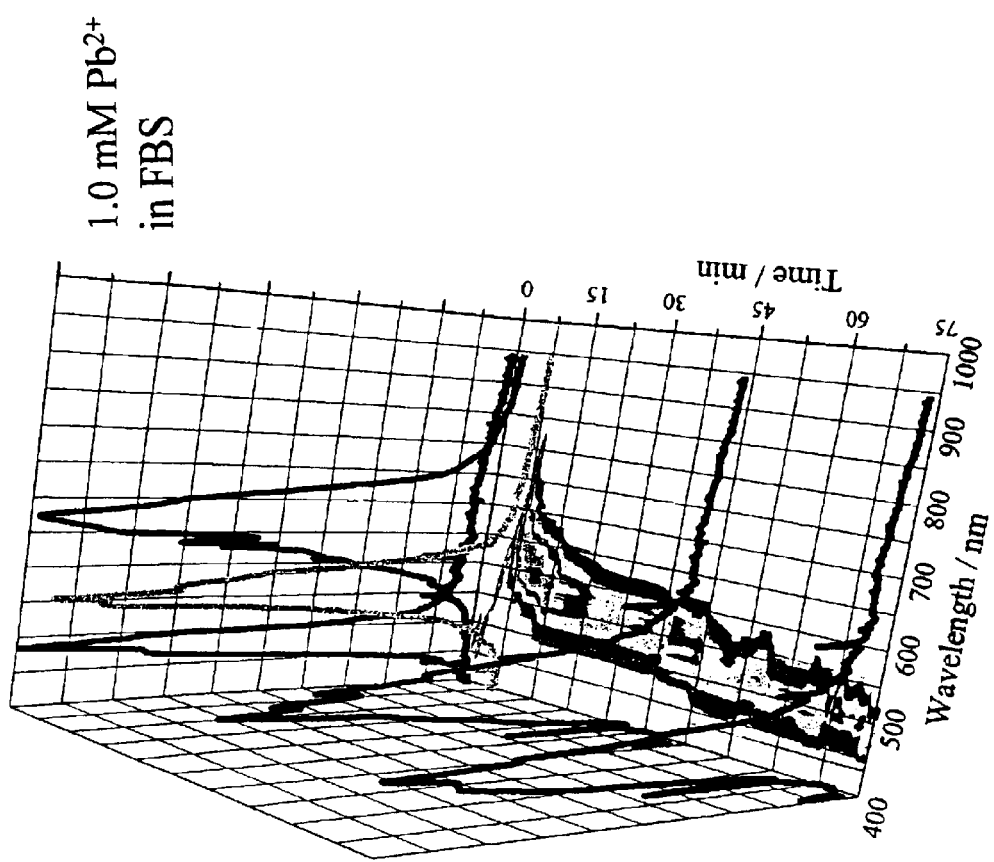
FIG. 13: Three-dimensional diffraction plot of the transient response of PCCA "C" incubated in pure fetal bovine serum, then exposed to a solution of 1.0 mM $Pb^{2+}$ fetal bovine serum, and then finally exposed to pure water.

FIG. 13 shows the transient response of PCCA "C", which was first incubated in pure fetal bovine serum, subsequently exposed to a solution of 1.0 mM $Pb^{2+}$ in fetal bovine serum, and then exposed to pure water. PCCA "C" diffracted at 481 nm in pure fetal bovine serum in the absence of $Pb^{2+}$. The fetal bovine serum solution was exchanged by a 1.0 mM $Pb^{2+}$ fetal bovine serum solution, and no significant shift was observed in the diffraction wavelength, indicating that the high ionic strength of the fetal bovine serum essentially prevents any PCCA response to the presence of $Pb^{2+}$. The exchange of the 1.0 mM $Pb^{2+}$ fetal bovine serum solution with pure water results in a large transient red shift, wherein the 680 nm maximum occurred in 5 minutes. PCCA "C" blue shifted back to 550 nm within 8 minutes and 483 nm in 60 minutes. Thus, the transient response time of PCCA "C" in fetal bovine serum is significantly slower than in the 100 mM NaCl solution discussed in previous Examples.

Figure 14:
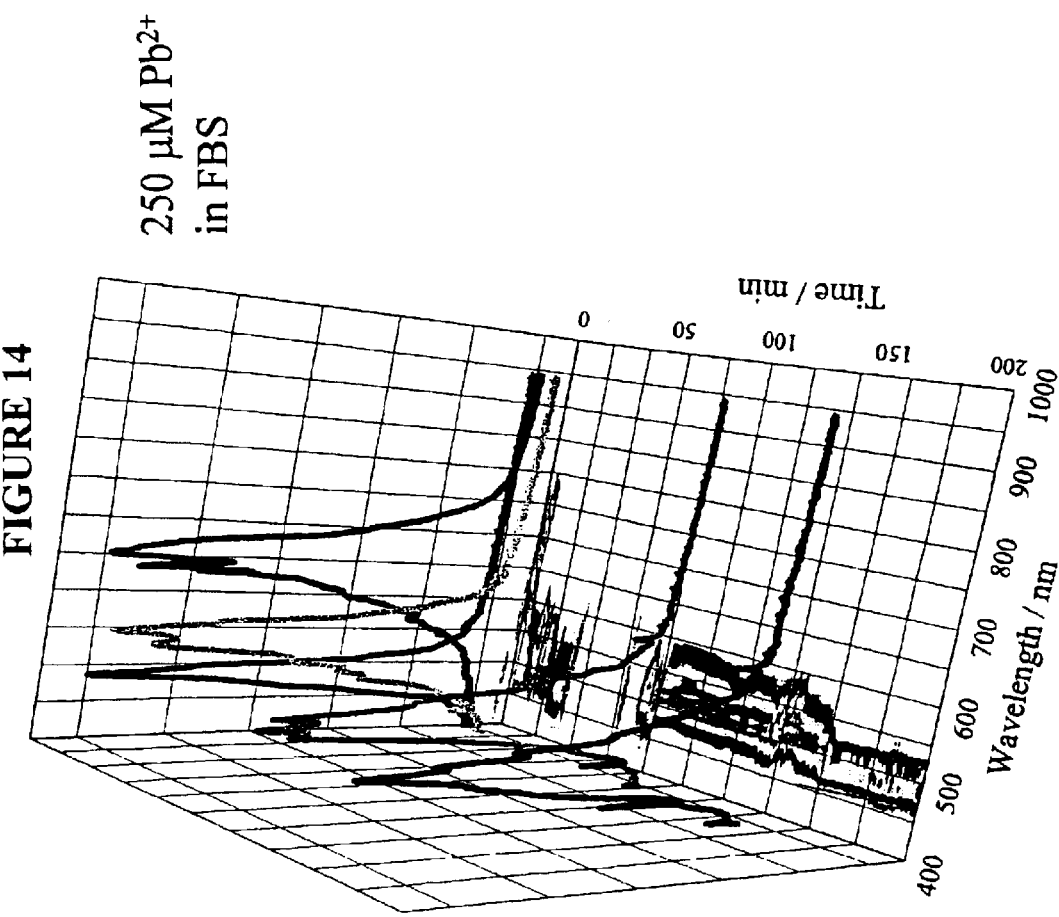
FIG. 14: Three-dimensional diffraction plot of the transient response of PCCA "C" incubated in a solution of 250 μM $Pb^{2+}$ fetal bovine serum to pure water.

FIG. 14 shows a similar set of measurements wherein PCCA "C" was placed in a solution of 250 $\mu$M $Pb^{2+}$ in fetal bovine serum. PCCA "C" initially diffracted at 480 nm in both the pure fetal bovine serum and the 250 $\mu$M $Pb^{2+}$ fetal bovine serum solution. PCCA "C" was subsequently exposed to pure water, and a transient red shift to a maximum of 667 nm was observed within 5 minutes. By t=160 minutes, the diffraction peak had blue shifted almost completely back to the value in pure water of 487 nm.

Figure 15:
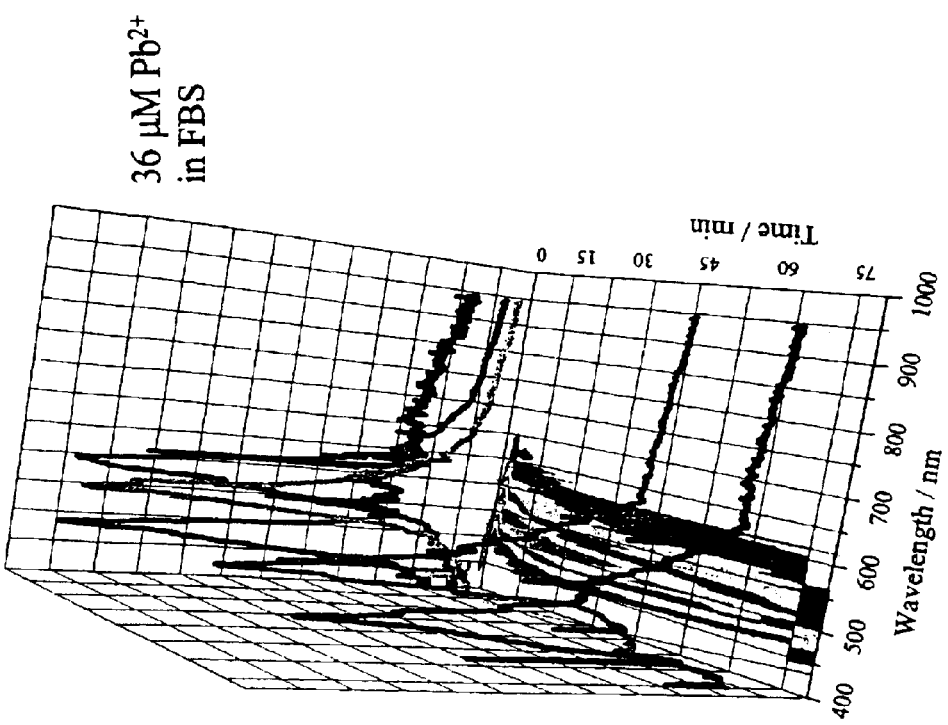
FIG. 15: Three-dimensional diffraction plot of the transient response of PCCA "C" incubated in a solution of 36 μM $Pb^{2+}$ fetal bovine serum to pure water.

FIG. 15 shows the transient response of PCCA "C" in a lower concentration solution of 36 $\mu$M $Pb^{2+}$ in fetal bovine serum. PCCA "C" initially diffracted at 480 nm in both the pure fetal bovine serum and the 36 $\mu$M $Pb^{2+}$ fetal bovine serum solution. Upon exposing PCCA "C" to pure water, the hydrogel transiently red shifted to a maximum of 600 nm within 5 minutes. By t=70 minutes, the diffraction peak blue shifted almost completely back to the initial diffraction at 485 $\mu$m.

Figure 16:
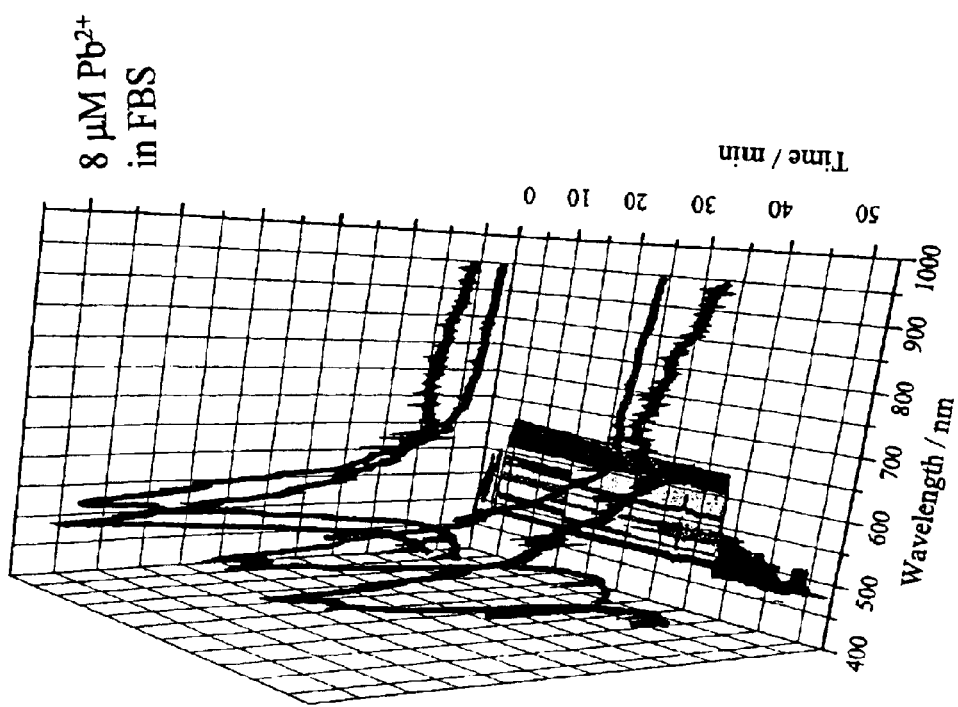
FIG. 16: Three-dimensional diffraction plot of the transient response of PCCA "C" incubated in a solution of 8 μM $Pb^{2+}$ fetal bovine serum to pure water.

FIG. 16 shows PCCA diffraction results in an even lower concentration solution of 8 $\mu$M $Pb^{2+}$ in fetal bovine serum. PCCA "C" initially diffracted at 480 nm in both the pure fetal bovine serum as well as the 8 $\mu$M $Pb^{2+}$ fetal bovine serum solution. Upon exposure to pure water, PCCA "C" transiently red shifted to a maximum value of 532 nm within 5 minutes. After 40 minutes, PCCA "C" blue shifted back to its value in pure water of ~480 nm.

Figure 17:
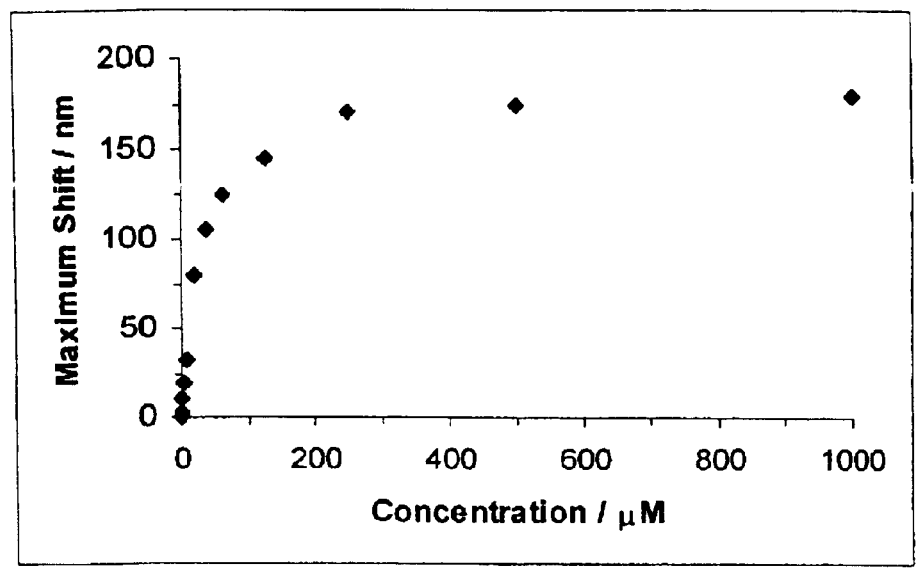
FIG. 17: (A) Plot of the concentration dependence of the maximum transient diffraction wavelength shift observed for PCCA "C" at various $Pb^{2+}$ concentrations in fetal bovine serum; (B) Expanded plot of the concentration dependence of the maximum transient diffraction wavelength shift observed for PCCA "C" at $Pb^{2+}$ concentrations in fetal bovine serum between 0 and 36 $\mu$M. The detection limit is less than 0.5 $\mu$M $Pb^{2+}$ concentration, and the best fit line is shown.
Figure 17:
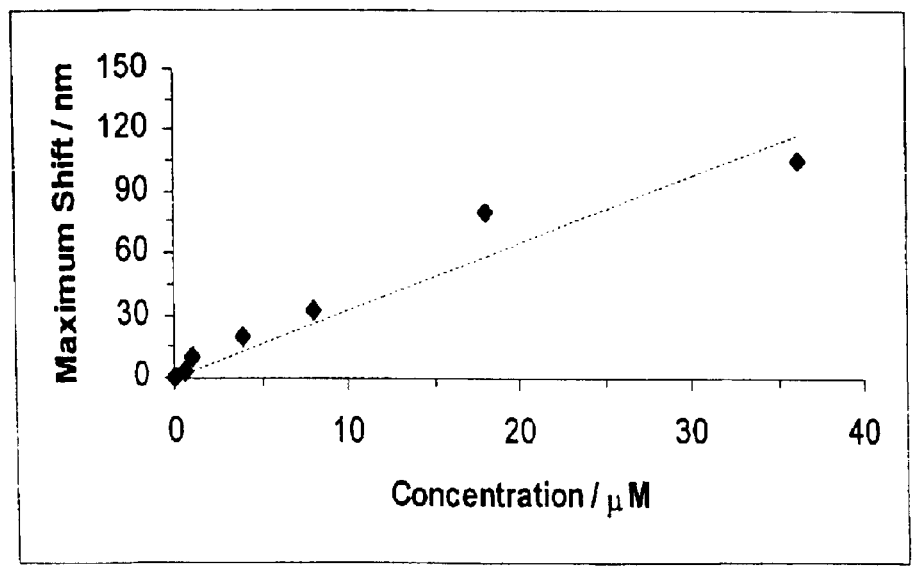

After diffraction results were obtained from several other solutions containing fetal bovine serum at varying concentrations of $Pb^{2+}$, a plot was made of the $Pb^{2+}$ concentration dependence of the maximum transient diffraction red shift observed for each one of the solutions of fetal bovine serum (FIG. 17(A)). FIG. 17(B) shows an expanded plot of the lower $Pb^{2+}$ concentrations from FIG. 17(A). The maximum transient shifts used to make these plots were first corrected by subtracting the ~20 nm red shift of the PCCA due to pure fetal bovine serum where no $Pb^{2+}$ present. For example, the 3 nm transient shift response reported in the plots for a fetal bovine serum solution containing 0.5 $\mu$M $Pb^{2+}$ was actually a 23 nm total red Because the standard deviation in the detected wavelength shift is ~1 nm, this indicates a detection limit of less than 500 nM $Pb^{2+}$. Thus, it is possible to detect, for example, the presence of $Pb^{2+}$ at concentrations of 0.48 $\mu$M. This is important because United States and international guidelines recommend that $Pb^{2+}$ in bodily fluids should be measured with a detection limit of 0.48 $\mu$M.

FIGS. 17(A) and (B) show that the response of PCCA "C" to $Pb^{2+}$ in fetal bovine serum is quasi-exponential and saturates at concentrations above ~100 $\mu$M $Pb^{2+}$, where the crown ether binding sites become saturated.

We claim:

1. A method for detecting the concentration of a chemical species in a high ionic strength solution comprising:

preparing a sensor device comprising a crystalline colloidal array polymerized in a hydrogel that undergoes a volume change in response to said chemical species, said crystalline colloidal array having a lattice spacing that changes when said volume of said hydrogel changes, thereby causing the diffracted wavelength of the crystalline colloidal array to change;

equilibrating said sensor device in said high ionic strength solution;

measuring the diffracted wavelength of said crystalline colloidal array following equilibration in the high ionic strength solution;

removing said sensor device from said high ionic strength solution and immediately immersing said sensor device in a low ionic strength solution;

measuring the maximum transient diffracted wavelength of said crystalline colloidal array following said immersion in the low ionic strength solution; and comparing the change in diffracted wavelength measurements to determine the concentration of said chemical species in said high ionic strength solution.

2. The method of claim 1, including employing the use of a detection device to determine said diffracted wavelength change.

3. The method of claim 2 wherein said detection device is selected from the group consisting of a spectrometer or a spectrophotometer.

4. The method of claim 1 wherein said high ionic strength solution is selected from the group consisting of bodily fluids, ground water, and waste storage samples.

5. The method of claim 1 wherein said low ionic strength solution is pure water.

6. The method of claim 1 wherein said low ionic strength solution is selected from the group consisting of dimethyl sulfoxide and a mixture of pure water and dimethyl sulfoxide.

7. The method of claim 1, including employing the unassisted human eye to determine said diffracted wavelength change, wherein such a change is detectable by a change in color of the sensor device.

8. The method of claim 1, wherein said sensor device preparation step includes the steps of:

a) allowing charged colloidal particles to self-assemble into a crystalline colloidal array;

b) adding a first comonomer that is a gel monomer, a crosslinking agent, a second comonomer capable of molecular recognition, and a polymerization initiator to a medium comprising said crystalline colloidal array; and c) polymerizing the mixture of step b) to form a crystalline colloidal array embedded in a hydrogel.

9. The method of claim 8, including employing a medium that is hydrophilic.

10. The method of claim 8, including employing a gel monomer that is an ion-free gel.

11. The method of claim 8, including employing a gel monomer selected from the group consisting of acrylamide gels, purified agarose gels, N-vinylpyrolidone gels, polyvinyl alcohol gels, and methacrylate gels.

12. The method of claim 8, including employing a molecular recognition monomer selected from the group consisting of crown ethers, cyclodextrans, caloxarenes, glucose oxidase, complimentary DNA molecules, and antigens.

13. The method of claim 12, including employing a 4-acryloylamidobenzo-18-crown-6 ether.

14. The method of claim 8, including employing a crosslinking agent selected from the group consisting of N,N'-methylenebisacrylamide, methylenebismethacrylamide and ethyleneglycol-dimethacrylate.

15. The method of claim 8, including employing charged particles selected from the group consisting of colloidal polystyrene, polymethylmethacrylate, silicon dioxide, aluminum oxide, polytetrafluoroethylene and poly N-isopropylacrylamide.

* * * * *